United States Patent
Bachmann

(10) Patent No.: US 10,246,516 B2
(45) Date of Patent: Apr. 2, 2019

(54) ANTI-LA ANTIBODIES AND THEIR USE FOR IMMUNOTARGETING

(71) Applicant: GEMoaB Monoclonals GmbH, Dresden (DE)

(72) Inventor: Michael Bachmann, Kelkheim (DE)

(73) Assignee: GEMoaB Monoclonals GmbH, Dresden (DE)

( * ) Notice: Subject to any disclaimer, the term of this patent is extended or adjusted under 35 U.S.C. 154(b) by 216 days.

(21) Appl. No.: 15/355,060

(22) Filed: Nov. 18, 2016

(65) Prior Publication Data

US 2017/0158774 A1 Jun. 8, 2017

Related U.S. Application Data

(62) Division of application No. 13/814,510, filed as application No. PCT/EP2011/063539 on Aug. 5, 2011, now Pat. No. 9,540,446.

(30) Foreign Application Priority Data

Aug. 6, 2010 (DE) ........................ 10 2010 039 018

(51) Int. Cl.
  *C07K 16/30* (2006.01)
  *C07K 16/28* (2006.01)
  *C07K 16/18* (2006.01)

(52) U.S. Cl.
  CPC .............. *C07K 16/30* (2013.01); *C07K 16/18* (2013.01); *C07K 16/2809* (2013.01); *C07K 2317/24* (2013.01); *C07K 2317/31* (2013.01); *C07K 2317/34* (2013.01); *C07K 2317/54* (2013.01); *C07K 2317/56* (2013.01); *C07K 2317/565* (2013.01); *C07K 2317/622* (2013.01); *C07K 2317/626* (2013.01); *C07K 2317/73* (2013.01)

(58) Field of Classification Search
  None
  See application file for complete search history.

(56) References Cited

U.S. PATENT DOCUMENTS

| | | | |
|---|---|---|---|
| 4,699,784 A | 10/1987 | Shih et al. | |
| 4,751,181 A | 6/1988 | Keene | |
| 4,784,942 A | 11/1988 | Harley | |
| 5,457,029 A | 10/1995 | Coppel et al. | |
| 2005/0136050 A1 | 6/2005 | Kufer et al. | |

FOREIGN PATENT DOCUMENTS

| | | |
|---|---|---|
| WO | 2000/037503 A1 | 6/2000 |
| WO | 2008/043148 A1 | 4/2008 |

OTHER PUBLICATIONS

Mattiolli M. et al.: Heterogeniety of RNA Protein Antigens Reactive with Sera of Patients with Systemic Lupus Erythematosus; Arthritis and Rheumatism, vol. 17, No. 4, pp. 421ff (1974); cited in specification, p. 1, 2nd paragraph.
Alspaugh M. A. et al.: Antibodies to Cellular Antigens in Sjögren's Syndrome; The Journal of Clinical Investigation, vol. 55, pp. 1067ff (1975); cited in specification, p. 1, 2nd paragraph.
Gottlieb E. et al.: The RNA binding protein La influences both the accuracy and the efficeincy of RNA polymerase III transcription in vitro, The EMBo Journal, vol. 9, No. 3, pp. 841ff (1989); cited in specification, p. 1, 3rd paragraph.
Chambers J. C. et al.: Genornic Structure and Amino Acid Sequence Domains of the Human La Auloantigen; The Journal of Biological Chemistry; vol. 263, No. 34, pp. 18043ff (1988); cited in specification, p. 1, 4th paragraph.
McNeilage L. J. et al.: Molecular analysis of the RNA and protein components recognized by anti-LA(SSB) autoantibodies; Clin. exp. Immunol. (1985) 62, 685-694; cited in specification, paragraph bridging pp. 1 and 2.
Scofiled R. H. et al.: Fine specificity of the autoimmune repsonse to the Ro/SSA and La/SSB ribonucleoproteins; Arthritis & Rheumatism vol. 42, No. 2, Feb. 1999, pp. 199-209; cited in specification, paragraph bridging pp. 1 and 2.
Chan E. K. L. et al.: Human autoantibody-reactive epitopes of SS-B/La are highly conserved in comparison with epitopes recognized by murine monoclonal antibodies; J. Exp. Med., vol. 166, Dec. 1987, pp. 1627ff; cited in specification, p. 2, 1st full paragraph.
Bachmann M. et al.: Shuttling of the Autoaritgen La between Nucleus and Cell Surface after uv Irradiation of Human Keratinocytes; Experimental Cell Research, 191, pp. 171-180 (1990); cited in specification, p. 2, 2nd full paragraph.
Smith P. R. et al.: Monoclonal Antibodies to the Sjögren's Syndrome Associated Antigen SS-B (La): Journal of Immunological Methods, 77 (1985) 63-76; cited in specification, p. 2, lines 21-22, p. 3, line 5.

(Continued)

*Primary Examiner* — G. R. Ewoldt
(74) *Attorney, Agent, or Firm* — FisherBroyles, LLP; Andrew K. Gonsalves, Esq.

(57) ABSTRACT

The invention relates to antibodies against the human La protein and to their use in immunotargeting, in particular the immunotargeting of tumor cells. The object of the invention is to provide improved antibodies which bind universal target structures on the surface of tumor cells, and to provide novel anti-La antibodies, in particular with a high affinity for La, a universal target structure on tumor cells, which make it possible to use the antibodies as recombinant fragments for immunotargeting. The invention comprises recombinant antibodies comprising: (i) a binding unit of an antibody which specifically binds to an epitope of a human nuclear antigen, preferably human La protein, and (ii) a binding unit of an antibody which specifically binds to an effector cell or of a ligand which specifically binds to an effector cell. The invention furthermore comprises novel antibodies which specifically bind the human La protein.

7 Claims, 13 Drawing Sheets

Specification includes a Sequence Listing.

(56) References Cited

OTHER PUBLICATIONS

Mamula M. J. et al.: Human Monoclonal Anti-La Antibodies; The Journal of Immunology, vol. 143; No. 9, pp. 2923-2928 (Nov. 1, 1989); cited in specification, p. 2, lines 24-25, p. 3, line 2.

Offen D. et al.: Monoclonal Anti-La Antibody Derived from a Mouse with Experimental SLE is similar to Human Anti-La Antibodyies; Journal of Autoimmunity (1990) 3, 701-713; cited in specification, p. 2, lines 27-28.

Bachmann M. et al.: Association of La and Ro antigens with intracellular structures in HEp-2 carcinoma cells; Proc. Natl. Acad Sci USA, vol. 83, pp. 7770-7774, Oct. 1986; cited in specification, p. 3, line 1.

Carmo-Fonseca M. et al.: Identification of La Ribonucleoproteins as a Component of Interchromatin Granules; Experimental Cell Research; 185 (1989) 73-85; cited in specification, p. 3, line 3.

Tröster H. et al.: Activation of Murine Autoreactive B cell by Immunization with Human Recombinant Autoantigen La/SS-B: Characterization of the Autoepitope, Journal of Autoimmunity (1995) 8, 825-842; cited in specification, p. 3, line 4.

Pruijn G. J. M. et al.: Anti-La monoclonal antibodies recognizing epitopes within the RNA-binding domains of the La protein show differential capacities to immunoprecipitae RNA-associated La protein; Eur. J. Biochem. 232, 611-619 (1995); cited in specification, p. 3, line 6.

Tran H. B. et al.: Subcellular Reditribution of La/SSB Autoantigen During Phydsiologioc Apoptosis in the Fetal Mouse Heart and Conduction System; Arthritis & Rheumatism vol. 46, No. 1, Jan. 2002, pp. 202-208; cited in specification, p. 3, line 7.

Al-Ejeh F. et al.: A simplified suite of methods to evaluate chelator conjugation of antibodies: effects on hydrodyriatnic radius and biodistribution; Nuclear Medicine and Biology; 36 (2009) 395-402, cited in specification, p. 3, line 8.

Al-Ejeh F. et al.: The La Auloarifigen is a Maligrianc-Associated Cell Death Target That Is Induced by DNA-Damaging Drugs; Clin. Cancer Res. 2007; 13 (18 Suppl) Sep. 15, 2007; pp. 5509s ff.; see international search report; cited in specification, p. 3, line 15.

Alejeh F. et al.: In vivo Targeting of Dead Tumor Cells in Murine Tumor Model Using a Monoclonal Antibody Specific for the La Autoantigen; Clin. Cancer Res. 2007; 13 (16 Supp) Sep. 15, 2007; pp. 5519s ff.; see international search report; cited in specification, p. 3, lines18/19.

Al-Ejeh F. et al.: Chemotherapy Synergizes with Radioimmunotherapy Targeting La Autoantigen in Tumors; PLOS ONE 4(2): e-4630: Feb. 2009; cited in specification, p. 3, line 21.

Alejeh F. et al.: APOMAD(R), a La-Specific Monoclonal Antibody, Detects the Apoptic Tumor Response to Life Prolonging and DNA-Damaging Chemotherapy; PLOS ONE 4(2): e4558; Feb. 2009; cited in specification, p. 3, line 25.

Bargou R. et al.: Tumor Regression in Cancer Patients by Very Low Doses of a T Cell-Engaging Antibody; Science; vol. 321, pp. 974 1f (Aug. 15, 2003); see international search report; cited in specification, p. 5, lines 9-11.

Brischwein K. et al.: A novel bispecific single-chain antibody construct with high efficacy in eradicating established tumors; Molecular Immunology 43 (2006) 1129-1143; cited in specification, p. 5, lines 11-13.

Baeuerle P. A. et al.: Bispecific T-Cell Engaging Antibodies for Cancer Therapy; Cancer Res. 2009; 69; (12); pp. 4941ff; Jun. 15, 2009; see international search report.

Baeuerle P. A. et al.: BiTE Teaching antibodies to engage T-cells for cancer therapy; Current Opinion in Molecular Therapy, 2009, 11(1); pp. 22-30; see international search report.

Bachmann M. et al.: Translocation of the Nuclear Autoantigen La to the Cell Surface of Herpes Simplex Virus Type 1 Infected Cells; Autoimmunity, 1992; vol. 12, pp. 37-45 see international search report.

Bachmann M. et al.: Translocation of the Nuclear Autoantigen La to Cell Surface: Assembly and Disassembly with the Extarcellular Matrix; Autoimmunity, 1991, vol. 9, pp. 99-107.

McNeilage L. J. et al.: Autoantibodies reactive with small ribonucloprotein antigens: a convergence of molecular biology and clinical immunology; J. Clin Lab. Immunol. (1984) vol. 15, pp. 1-17.

Raats J. M. H. et al.: Human recombinant anti-La (SS-B) autoantibodies demonstrate the accumulation of phosphoserine-366-containing La isoforms in nucleoplasmic speckles; European Journal of Cell Biology 82, pp. 131-141 (Mar. 2003).

Gonzalez et al.: NKG2D ligands: key targets of the immune response; Trends Immunol., 29(8):397-403 (2008).

Kontermann, R.E.: Recombinant bispecific antibodies for cancer therapy; Acta Pharmacologica Sinica, 26(1):1-9 (2005).

Kuroki et al.: Re-targeting of Cytotoxic T Lymphocytes and/or Natural Killer Cells to CEA-expressing Tumor Cells with Anti-CEA Antibody Activity; Anticancer Research, 25:3725-3732 (2005).

Moretta et al.: Activating receptors and coreceptors involved in human natural killer cell-mediated cytolysis; Annu Rev Immunol., 19:197-223 (2001).

Peipp et al.: Bispecific antibodies targeting cancer cells; Biochem Soc Trans., 30(4):507-511 (2002).

Rajalingam, R.: Human diversity of killer cell immunoglobulin-like receptors and disease; The Koreean J. Hematology, 46(4):216-228 (2011).

Chames et al.: Bispecific antibodies for cancer therapy: The light at the end of the tunnel?; Landes Bioscience, I (6):539-547 (2009).

| | | | | SEQ ID NO: |
|---|---|---|---|---|
| La (NM_003142) | (AA301) | VTWEVLEGEVEKEALKKIIEDQQESLNKWKEGRFKSKGRFKGKGKGNK | (AA350) | 86 |
| La AA303-344 | | ---WEVLEGEVEKEALKKIIEDQQESLNKWKSKGRFKGKGKGNK------ | +  | 87 |
| La AA303-338 | | ---WEVLEGEVEKEALKKIIEDQQESLNKWKSKGRFKG------------ | +  | 88 |
| La AA303-333 | | ---WEVLEGEVEKEALKKIIEDQQESLNKWKSKG---------------- | +  | 89 |
| La AA303-331 | | ---WEVLEGEVEKEALKKIIEDQQESLNKWKS------------------ | +  | 90 |
| La AA306-329 | | ------LEGEVEKEALKKIIEDQQESLNKW-------------------- | +  | 91 |
| La AA309-333 | | ---------EVEKEALKKIIEDQQESLNKWKSKG---------------- | +  | 92 |
| La AA309-329 | | ---------EVEKEALKKIIEDQQESLNKW-------------------- | +  | 93 |
| La AA309-323 | | ---------EVEKEALKKIIEDQQ------------------------- | -  | 94 |
| La AA311-331 | | -----------EKEALKKIIEDQQESLNKWKS------------------ | +  | 95 |
| La AA311-328 | | -----------EKEALKKIIEDQQESLNK-------------------- | +/- | 96 |
| La AA311-327 | | -----------EKEALKKIIEDQQESLN--------------------- | +/- | 97 |
| La AA313-328 | | -------------EALKKIIEDQQESLNK-------------------- | -  | 98 |

Fig. 7

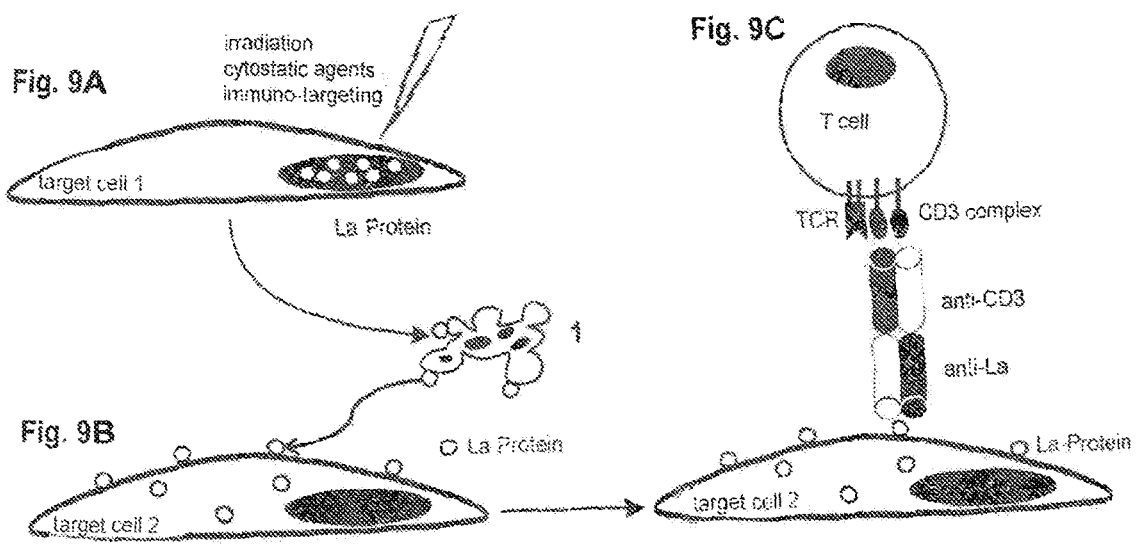

SEQUENCE LISTING

<160> NUMBER OF SEQ ID NOS: 98

<210> SEQ ID NO 1
<211> LENGTH: 408
<212> TYPE: PRT
<213> ORGANISM: Homo sapiens

<400> SEQUENCE: 1

```
Met Ala Glu Asn Gly Asp Asn Glu Lys Met Ala Ala Leu Glu Ala Lys
1               5                   10                  15

Ile Cys His Gln Ile Glu Tyr Tyr Phe Gly Asp Phe Asn Leu Pro Arg
                20                  25                  30

Asp Lys Phe Leu Lys Glu Gln Ile Lys Leu Asp Glu Gly Trp Val Pro
            35                  40                  45

Leu Glu Ile Met Ile Lys Phe Asn Arg Leu Asn Arg Leu Thr Thr Asp
        50                  55                  60

Phe Asn Val Ile Val Glu Ala Leu Ser Lys Ser Lys Ala Glu Leu Met
65                  70                  75                  80

Glu Ile Ser Glu Asp Lys Thr Lys Ile Arg Arg Ser Pro Ser Lys Pro
                85                  90                  95

Leu Pro Glu Val Thr Asp Glu Tyr Lys Asn Asp Val Lys Asn Arg Ser
            100                 105                 110

Val Tyr Ile Lys Gly Phe Pro Thr Asp Ala Thr Leu Asp Asp Ile Lys
        115                 120                 125

Glu Trp Leu Glu Asp Lys Gly Gln Val Leu Asn Ile Gln Met Arg Arg
    130                 135                 140

Thr Leu His Lys Ala Phe Lys Gly Ser Ile Phe Val Val Phe Asp Ser
145                 150                 155                 160

Ile Glu Ser Ala Lys Lys Phe Val Glu Thr Pro Gly Gln Lys Tyr Lys
                165                 170                 175

Glu Thr Asp Leu Leu Ile Leu Phe Lys Asp Asp Tyr Phe Ala Lys Lys
            180                 185                 190

Asn Glu Glu Arg Lys Gln Asn Lys Val Glu Ala Lys Leu Arg Ala Lys
        195                 200                 205

Gln Glu Gln Glu Ala Lys Gln Lys Leu Glu Glu Asp Ala Glu Met Lys
    210                 215                 220

Ser Leu Glu Glu Lys Ile Gly Cys Leu Leu Lys Phe Ser Gly Asp Leu
225                 230                 235                 240

Asp Asp Gln Thr Cys Arg Glu Asp Leu His Ile Leu Phe Ser Asn His
                245                 250                 255
```

```
Gly Glu Ile Lys Trp Ile Asp Phe Val Arg Gly Ala Lys Glu Gly Ile
            260                 265                 270

Ile Leu Phe Lys Glu Lys Ala Lys Glu Ala Leu Gly Lys Ala Lys Asp
        275                 280                 285

Ala Asn Asn Gly Asn Leu Gln Leu Arg Asn Lys Glu Val Thr Trp Glu
    290                 295                 300

Val Leu Glu Gly Glu Val Glu Lys Glu Ala Leu Lys Lys Ile Ile Glu
305                 310                 315                 320

Asp Gln Gln Glu Ser Leu Asn Lys Trp Lys Ser Lys Gly Arg Arg Phe
                325                 330                 335

Lys Gly Lys Gly Lys Gly Asn Lys Ala Ala Gln Pro Gly Ser Gly Lys
                340                 345                 350

Gly Lys Val Gln Phe Gln Gly Lys Lys Thr Lys Phe Ala Ser Asp Asp
            355                 360                 365

Glu His Asp Glu His Asp Glu Asn Gly Ala Thr Gly Pro Val Lys Arg
        370                 375                 380

Ala Arg Glu Glu Thr Asp Lys Glu Glu Pro Ala Ser Lys Gln Gln Lys
385                 390                 395                 400

Thr Glu Asn Gly Ala Gly Asp Gln
                405

<210> SEQ ID NO 2
<211> LENGTH: 13
<212> TYPE: PRT
<213> ORGANISM: Homo sapiens

<400> SEQUENCE: 2

Ser Lys Gly Arg Arg Phe Lys Gly Lys Gly Lys Gly Asn
1               5                   10

<210> SEQ ID NO 3
<211> LENGTH: 17
<212> TYPE: PRT
<213> ORGANISM: Mus musculus

<400> SEQUENCE: 3

Lys Ser Ser Gln Ser Leu Leu Asn Ser Arg Thr Pro Lys Asn Tyr Leu
1               5                   10                  15

Ala

<210> SEQ ID NO 4
<211> LENGTH: 5
<212> TYPE: PRT
<213> ORGANISM: Mus musculus

<400> SEQUENCE: 4

His Tyr Tyr Ile Tyr
1               5

<210> SEQ ID NO 5
<211> LENGTH: 7
<212> TYPE: PRT
<213> ORGANISM: Mus musculus

<400> SEQUENCE: 5

Trp Ala Ser Thr Arg Lys Ser
1               5

<210> SEQ ID NO 6
```

```
<211> LENGTH: 17
<212> TYPE: PRT
<213> ORGANISM: Mus musculus

<400> SEQUENCE: 6

Gly Val Asn Pro Ser Asn Gly Gly Thr His Phe Asn Glu Lys Phe Lys
1               5                   10                  15

Ser

<210> SEQ ID NO 7
<211> LENGTH: 8
<212> TYPE: PRT
<213> ORGANISM: Mus musculus

<400> SEQUENCE: 7

Lys Gln Ser Tyr Asn Leu Leu Thr
1               5

<210> SEQ ID NO 8
<211> LENGTH: 11
<212> TYPE: PRT
<213> ORGANISM: Mus musculus

<400> SEQUENCE: 8

Ser Glu Tyr Asp Tyr Gly Leu Gly Phe Ala Tyr
1               5                   10

<210> SEQ ID NO 9
<211> LENGTH: 17
<212> TYPE: PRT
<213> ORGANISM: Mus musculus

<400> SEQUENCE: 9

Arg Ser Ser Gln Ser Leu Leu Asp Ser Arg Thr Arg Lys Asn Tyr Leu
1               5                   10                  15

Ala

<210> SEQ ID NO 10
<211> LENGTH: 5
<212> TYPE: PRT
<213> ORGANISM: Mus musculus

<400> SEQUENCE: 10

Asp Phe Trp Met Asn
1               5

<210> SEQ ID NO 11
<211> LENGTH: 7
<212> TYPE: PRT
<213> ORGANISM: Mus musculus

<400> SEQUENCE: 11

Trp Ala Ser Thr Arg Glu Ser
1               5

<210> SEQ ID NO 12
<211> LENGTH: 19
<212> TYPE: PRT
<213> ORGANISM: Mus musculus

<400> SEQUENCE: 12

Gln Ile Arg Asn Lys Pro Asn Asn Tyr Glu Thr Tyr Tyr Ser Asp Ser
1               5                   10                  15
```

Leu Lys Gly

<210> SEQ ID NO 13
<211> LENGTH: 8
<212> TYPE: PRT
<213> ORGANISM: Mus musculus

<400> SEQUENCE: 13

Lys Gln Ser Tyr Asn Leu Pro Thr
1               5

<210> SEQ ID NO 14
<211> LENGTH: 8
<212> TYPE: PRT
<213> ORGANISM: Mus musculus

<400> SEQUENCE: 14

Leu Gly Asn Ser Trp Phe Ala Tyr
1               5

<210> SEQ ID NO 15
<211> LENGTH: 10
<212> TYPE: PRT
<213> ORGANISM: Mus musculus

<400> SEQUENCE: 15

Ser Ala Ser Ser Ser Val Ser Tyr Met Tyr
1               5                   10

<210> SEQ ID NO 16
<211> LENGTH: 5
<212> TYPE: PRT
<213> ORGANISM: Mus musculus

<400> SEQUENCE: 16

Asn Tyr Tyr Ile Tyr
1               5

<210> SEQ ID NO 17
<211> LENGTH: 7
<212> TYPE: PRT
<213> ORGANISM: Mus musculus

<400> SEQUENCE: 17

Asp Thr Ser Lys Leu Ala Ser
1               5

<210> SEQ ID NO 18
<211> LENGTH: 17
<212> TYPE: PRT
<213> ORGANISM: Mus musculus

<400> SEQUENCE: 18

Tyr Ile Tyr Pro Gly Asn Gly Gly Thr Ala Tyr Asn Gln Lys Phe Lys
1               5                   10                  15

Asp

<210> SEQ ID NO 19
<211> LENGTH: 8
<212> TYPE: PRT
<213> ORGANISM: Mus musculus

<400> SEQUENCE: 19

Gln Gln Trp Ser Ser Asn Pro Gln

```
<210> SEQ ID NO 20
<211> LENGTH: 10
<212> TYPE: PRT
<213> ORGANISM: Mus musculus

<400> SEQUENCE: 20

Arg Gly Ala Leu Gly Tyr Tyr Phe Asp Tyr
1               5                   10

<210> SEQ ID NO 21
<211> LENGTH: 10
<212> TYPE: PRT
<213> ORGANISM: Mus musculus

<400> SEQUENCE: 21

Ser Ala Ser Ser Ser Val Ser Tyr Met His
1               5                   10

<210> SEQ ID NO 22
<211> LENGTH: 5
<212> TYPE: PRT
<213> ORGANISM: Mus musculus

<400> SEQUENCE: 22

Asn Tyr Gly Ile Ser
1               5

<210> SEQ ID NO 23
<211> LENGTH: 7
<212> TYPE: PRT
<213> ORGANISM: Mus musculus

<400> SEQUENCE: 23

Asp Thr Ser Lys Leu Ala Ser
1               5

<210> SEQ ID NO 24
<211> LENGTH: 17
<212> TYPE: PRT
<213> ORGANISM: Mus musculus

<400> SEQUENCE: 24

Glu Ile Tyr Arg Gly Ser Gly Asn Ser Tyr Tyr Asn Glu Lys Phe Lys
1               5                   10                  15
Gly

<210> SEQ ID NO 25
<211> LENGTH: 9
<212> TYPE: PRT
<213> ORGANISM: Mus musculus

<400> SEQUENCE: 25

Gln Gln Trp Ile Ser Asn Pro Pro Thr
1               5

<210> SEQ ID NO 26
<211> LENGTH: 7
<212> TYPE: PRT
<213> ORGANISM: Mus musculus

<400> SEQUENCE: 26

Gly Gly Leu Ser Phe Ala Tyr
```

<210> SEQ ID NO 27
<211> LENGTH: 11
<212> TYPE: PRT
<213> ORGANISM: Mus musculus

<400> SEQUENCE: 27

Arg Ala Ser Glu Asn Ile Tyr Thr Tyr Leu Ala
1               5                   10

<210> SEQ ID NO 28
<211> LENGTH: 5
<212> TYPE: PRT
<213> ORGANISM: Mus musculus

<400> SEQUENCE: 28

Asp Tyr Trp Ile Glu
1               5

<210> SEQ ID NO 29
<211> LENGTH: 7
<212> TYPE: PRT
<213> ORGANISM: Mus musculus

<400> SEQUENCE: 29

Asn Ala Lys Thr Leu Ala Glu
1               5

<210> SEQ ID NO 30
<211> LENGTH: 17
<212> TYPE: PRT
<213> ORGANISM: Mus musculus

<400> SEQUENCE: 30

Glu Ile Leu Pro Gly Ser Val Ser Ile Lys Tyr Asn Glu Lys Phe Lys
1               5                   10                  15

Gly

<210> SEQ ID NO 31
<211> LENGTH: 9
<212> TYPE: PRT
<213> ORGANISM: Mus musculus

<400> SEQUENCE: 31

Gln His His Tyr Gly Thr Pro Tyr Thr
1               5

<210> SEQ ID NO 32
<211> LENGTH: 11
<212> TYPE: PRT
<213> ORGANISM: Mus musculus

<400> SEQUENCE: 32

Ser Arg Ser Ile Tyr Asp Gly Tyr Phe Tyr Tyr
1               5                   10

<210> SEQ ID NO 33
<211> LENGTH: 10
<212> TYPE: PRT
<213> ORGANISM: Mus musculus

<400> SEQUENCE: 33

Ser Ala Ser Ser Ser Val Ser Tyr Met Tyr

```
1               5                   10

<210> SEQ ID NO 34
<211> LENGTH: 5
<212> TYPE: PRT
<213> ORGANISM: Mus musculus

<400> SEQUENCE: 34

Ser Tyr Gly Ile Asn
1               5

<210> SEQ ID NO 35
<211> LENGTH: 7
<212> TYPE: PRT
<213> ORGANISM: Mus musculus

<400> SEQUENCE: 35

Arg Thr Ser Asn Leu Glu Ser
1               5

<210> SEQ ID NO 36
<211> LENGTH: 17
<212> TYPE: PRT
<213> ORGANISM: Mus musculus

<400> SEQUENCE: 36

Glu Ile Tyr Pro Gly Ser Gly Thr Thr Phe Tyr Asn Glu Lys Phe Arg
1               5                   10                  15

Gly

<210> SEQ ID NO 37
<211> LENGTH: 9
<212> TYPE: PRT
<213> ORGANISM: Mus musculus

<400> SEQUENCE: 37

Gln Gln Tyr His Ser Tyr Pro Arg Thr
1               5

<210> SEQ ID NO 38
<211> LENGTH: 10
<212> TYPE: PRT
<213> ORGANISM: Mus musculus

<400> SEQUENCE: 38

His Gly Gly Tyr Pro Phe Tyr Phe Asp Tyr
1               5                   10

<210> SEQ ID NO 39
<211> LENGTH: 15
<212> TYPE: PRT
<213> ORGANISM: Mus musculus

<400> SEQUENCE: 39

Arg Ala Ser Glu Ser Val Asp Ser Tyr Gly Asn Ser Phe Met His
1               5                   10                  15

<210> SEQ ID NO 40
<211> LENGTH: 7
<212> TYPE: PRT
<213> ORGANISM: Mus musculus

<400> SEQUENCE: 40

Thr Ser Gly Met Gly Val Ser
```

```
<210> SEQ ID NO 41
<211> LENGTH: 7
<212> TYPE: PRT
<213> ORGANISM: Mus musculus

<400> SEQUENCE: 41

Arg Ala Ser Asn Leu Glu Ser
1               5

<210> SEQ ID NO 42
<211> LENGTH: 16
<212> TYPE: PRT
<213> ORGANISM: Mus musculus

<400> SEQUENCE: 42

His Ile Tyr Trp Asp Asp Asp Lys Gly Tyr Asn Pro Ser Leu Lys Ser
1               5                   10                  15

<210> SEQ ID NO 43
<211> LENGTH: 9
<212> TYPE: PRT
<213> ORGANISM: Mus musculus

<400> SEQUENCE: 43

Gln Gln Ser Asn Glu Asp Pro Pro Thr
1               5

<210> SEQ ID NO 44
<211> LENGTH: 7
<212> TYPE: PRT
<213> ORGANISM: Mus musculus

<400> SEQUENCE: 44

Gly Asp Val Glu Phe Asp Tyr
1               5

<210> SEQ ID NO 45
<211> LENGTH: 10
<212> TYPE: PRT
<213> ORGANISM: Mus musculus

<400> SEQUENCE: 45

Ser Ala Ser Ser Ser Val Ser Tyr Met Tyr
1               5                   10

<210> SEQ ID NO 46
<211> LENGTH: 5
<212> TYPE: PRT
<213> ORGANISM: Mus musculus

<400> SEQUENCE: 46

Thr Tyr Gly Leu Thr
1               5

<210> SEQ ID NO 47
<211> LENGTH: 7
<212> TYPE: PRT
<213> ORGANISM: Mus musculus

<400> SEQUENCE: 47

Arg Thr Ser Asn Leu Glu Ser
1               5
```

<210> SEQ ID NO 48
<211> LENGTH: 17
<212> TYPE: PRT
<213> ORGANISM: Mus musculus

<400> SEQUENCE: 48

Glu Ile Phe Pro Gly Ser Gly Thr Thr Phe Tyr Asn Glu Lys Phe Asn
1               5                   10                  15

Asp

<210> SEQ ID NO 49
<211> LENGTH: 9
<212> TYPE: PRT
<213> ORGANISM: Mus musculus

<400> SEQUENCE: 49

Gln Gln Tyr His Ser Tyr Pro Arg Thr
1               5

<210> SEQ ID NO 50
<211> LENGTH: 10
<212> TYPE: PRT
<213> ORGANISM: Mus musculus

<400> SEQUENCE: 50

Tyr Ser Asn Tyr Pro Tyr Tyr Phe Asp Tyr
1               5                   10

<210> SEQ ID NO 51
<211> LENGTH: 112
<212> TYPE: PRT
<213> ORGANISM: Mus musculus

<400> SEQUENCE: 51

Ile Val Leu Thr Gln Thr Thr Ser Ser Leu Ala Val Ser Ala Gly Glu
1               5                   10                  15

Lys Val Thr Met Ser Cys Lys Ser Ser Gln Ser Leu Leu Asn Ser Arg
                20                  25                  30

Thr Pro Lys Asn Tyr Leu Ala Trp Tyr Gln Gln Lys Pro Gly Gln Ser
            35                  40                  45

Pro Lys Leu Leu Ile Tyr Trp Ala Ser Thr Arg Lys Ser Gly Val Pro
        50                  55                  60

Asp Arg Phe Thr Gly Ser Gly Ser Gly Thr Asp Phe Thr Leu Thr Ile
65                  70                  75                  80

Ser Ser Val Gln Ala Glu Asp Leu Ala Val Tyr Tyr Cys Lys Gln Ser
                85                  90                  95

Tyr Asn Leu Leu Thr Phe Gly Ala Gly Thr Lys Leu Glu Leu Lys Arg
            100                 105                 110

<210> SEQ ID NO 52
<211> LENGTH: 119
<212> TYPE: PRT
<213> ORGANISM: Mus musculus

<400> SEQUENCE: 52

Val Gln Leu Glu Glu Ser Gly Ala Glu Leu Val Lys Pro Gly Ala Ser
1               5                   10                  15

Val Lys Leu Ser Cys Lys Ala Ser Gly Tyr Ala Phe Thr His Tyr Tyr
                20                  25                  30

Ile Tyr Trp Ile Lys Gln Arg Pro Gly Gln Gly Leu Glu Trp Ile Gly

```
            35                  40                  45
Gly Val Asn Pro Ser Asn Gly Thr His Phe Asn Glu Lys Phe Lys
 50                  55                  60

Ser Lys Ala Thr Leu Thr Val Asp Lys Ser Ser Ser Thr Ala Tyr Met
 65                  70                  75                  80

Gln Leu Ser Ser Leu Thr Ser Glu Asp Ser Ala Val Tyr Tyr Cys Thr
                     85                  90                  95

Arg Ser Glu Tyr Asp Tyr Gly Leu Gly Phe Ala Tyr Trp Gly Gln Gly
                    100                 105                 110

Thr Leu Val Thr Val Ser Ala
                115

<210> SEQ ID NO 53
<211> LENGTH: 111
<212> TYPE: PRT
<213> ORGANISM: Mus musculus

<400> SEQUENCE: 53

Asp Ile Val Ile Thr Gln Ser Pro Ser Ser Leu Ala Val Ser Ala Gly
 1               5                  10                  15

Glu Lys Val Thr Met Ser Cys Arg Ser Ser Gln Ser Leu Leu Asp Ser
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Asn Val Gln Ala Glu Asp Leu Ala Val Tyr Tyr Cys Lys Gln
                     85                  90                  95

Ser Tyr Asn Leu Pro Thr Phe Gly Gly Gly Thr Lys Leu Glu Ile
                    100                 105                 110

<210> SEQ ID NO 54
<211> LENGTH: 116
<212> TYPE: PRT
<213> ORGANISM: Mus musculus

<400> SEQUENCE: 54

Val Lys Leu Gln Glu Ser Gly Gly Gly Leu Val Gln Pro Gly Arg Pro
 1               5                  10                  15

Met Lys Leu Ser Cys Val Ala Ser Gly Phe Thr Phe Ser Asp Phe Trp
                 20                  25                  30

Met Asn Trp Val Arg Gln Ser Pro Glu Lys Gly Leu Glu Trp Val Ala
             35                  40                  45

Gln Ile Arg Asn Lys Pro Asn Asn Tyr Glu Thr Tyr Tyr Ser Asp Ser
 50                  55                  60

Leu Lys Gly Arg Phe Thr Ile Ser Arg Asp Asp Ser Lys Ser Ser Val
 65                  70                  75                  80

Tyr Leu Gln Met Asn Asn Leu Arg Pro Glu Asp Met Gly Ile Tyr Tyr
                     85                  90                  95

Cys Thr Leu Gly Asn Ser Trp Phe Ala Tyr Trp Gly Gln Gly Thr Leu
                    100                 105                 110

Val Thr Val Ser
                115
```

```
<210> SEQ ID NO 55
<211> LENGTH: 106
<212> TYPE: PRT
<213> ORGANISM: Mus musculus

<400> SEQUENCE: 55

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Gln Phe
                85                  90                  95

Gly Thr Gly Thr Lys Leu Glu Val Lys Arg
            100                 105

<210> SEQ ID NO 56
<211> LENGTH: 119
<212> TYPE: PRT
<213> ORGANISM: Mus musculus

<400> SEQUENCE: 56

Gln Val Lys Leu Glu Glu Ser Gly Pro Glu Leu Val Lys Pro Gly Ala
1               5                   10                  15

Pro Val Lys Ile Ser Cys Lys Thr Ser Gly Tyr Thr Phe Thr Asn Tyr
            20                  25                  30

Tyr Ile Tyr Trp Val Lys Gln Arg Pro Gly Gln Gly Leu Glu Trp Ile
        35                  40                  45

Gly Tyr Ile Tyr Pro Gly Asn Gly Gly Thr Ala Tyr Asn Gln Lys Phe
    50                  55                  60

Lys Asp Lys Ala Thr Leu Thr Ala Asp Asn Pro Ser Asn Thr Ala Tyr
65                  70                  75                  80

Met Gln Leu Ser Ser Leu Thr Ser Glu Asp Ser Ala Val Tyr Leu Cys
                85                  90                  95

Ala Arg Arg Gly Ala Leu Gly Tyr Tyr Phe Asp Tyr Trp Gly Gln Gly
            100                 105                 110

Thr Thr Leu Thr Val Ser Ser
        115

<210> SEQ ID NO 57
<211> LENGTH: 107
<212> TYPE: PRT
<213> ORGANISM: Mus musculus

<400> SEQUENCE: 57

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60
```

```
Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ile Ser Asn Pro Pro Thr
                85                  90                  95

Phe Gly Gly Gly Thr Lys Leu Glu Ile Lys Arg
            100                 105

<210> SEQ ID NO 58
<211> LENGTH: 116
<212> TYPE: PRT
<213> ORGANISM: Mus musculus

<400> SEQUENCE: 58

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Ser Leu Thr Asn Tyr
            20                  25                  30

Gly Ile Ser Trp Val Lys Gln Arg Thr Gly Gln Gly Leu Glu Trp Ile
        35                  40                  45

Gly Glu Ile Tyr Arg Gly Ser Gly Asn Ser Tyr Tyr Asn Glu Lys Phe
    50                  55                  60

Lys Gly Lys Ala Ser Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Leu Ser Phe Ala Tyr Trp Gly Gln Gly Thr Leu Val
            100                 105                 110

Thr Val Ser Ala
        115

<210> SEQ ID NO 59
<211> LENGTH: 107
<212> TYPE: PRT
<213> ORGANISM: Mus musculus

<400> SEQUENCE: 59

Asp Ile Val Met Thr Gln Ser Thr Ala Ser Leu Ser Ala Ser Val Gly
1               5                   10                  15

Glu Thr Val Thr Ile Thr Cys Arg Ala Ser Glu Asn Ile Tyr Thr Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Arg Ile Asn Ser Leu Gln Pro
65                  70                  75                  80

Glu Asp Phe Gly Ser Tyr Tyr Cys Gln His Tyr Gly Thr Pro Tyr
                85                  90                  95

Thr Phe Gly Gly Gly Thr Lys Leu Glu Ile Lys
            100                 105

<210> SEQ ID NO 60
<211> LENGTH: 120
<212> TYPE: PRT
<213> ORGANISM: Mus musculus

<400> SEQUENCE: 60
```

Gln Val Lys Leu Gln Glu Ser Gly Ala Glu Leu Met Lys Pro Gly Ser
1               5                   10                  15

Ser Val Lys Phe Ser Cys Lys Ala Ala Gly Tyr Thr Phe Thr Asp Tyr
            20                  25                  30

Trp Ile Glu Trp Leu Lys Gln Arg Pro Gly His Gly Leu Glu Trp Ile
            35                  40                  45

Gly Glu Ile Leu Pro Gly Ser Val Ser Ile Lys Tyr Asn Glu Lys Phe
        50                  55                  60

Lys Gly Lys Ala Thr Phe Thr Ala Asp Thr Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Arg Ser Ile Tyr Asp Gly Tyr Phe Tyr Tyr Trp Gly Gln
            100                 105                 110

Gly Thr Thr Leu Thr Val Ser Ser
            115                 120

<210> SEQ ID NO 61
<211> LENGTH: 107
<212> TYPE: PRT
<213> ORGANISM: Mus musculus

<400> SEQUENCE: 61

Asp Ile Val Met Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Tyr Trp Tyr Gln Gln Lys Pro Gly Ser Ser Pro Lys Pro Trp Ile Tyr
            35                  40                  45

Arg Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Arg Thr
                85                  90                  95

Phe Gly Gly Gly Thr Lys Leu Glu Ile Lys Arg
            100                 105

<210> SEQ ID NO 62
<211> LENGTH: 118
<212> TYPE: PRT
<213> ORGANISM: Mus musculus

<400> SEQUENCE: 62

Val Gln Leu Gln Glu Ser Gly Ala Glu Leu Ala Arg Pro Gly Ala Ser
1               5                   10                  15

Val Lys Leu Ser Cys Lys Ala Ser Gly Tyr Ser Phe Arg Ser Tyr Gly
            20                  25                  30

Ile Asn Trp Val Lys Gln Arg Thr Gly Gln Gly Leu Glu Trp Ile Gly
            35                  40                  45

Glu Ile Tyr Pro Gly Ser Gly Thr Thr Phe Tyr Asn Glu Lys Phe Arg
        50                  55                  60

Gly Lys Ala Thr Leu Thr Ala Asp Lys Ser Ser Ser Thr Ala Tyr Met
65                  70                  75                  80

Gln Leu Lys Ser Leu Thr Ser Glu Asp Ser Ala Val Tyr Phe Cys Ala
                85                  90                  95

```
Arg His Gly Gly Tyr Pro Phe Tyr Phe Asp Tyr Trp Gly Gln Gly Thr
                100                 105                 110

Thr Leu Thr Val Ser Ser
        115

<210> SEQ ID NO 63
<211> LENGTH: 111
<212> TYPE: PRT
<213> ORGANISM: Mus musculus

<400> SEQUENCE: 63

Asp Ile Val Leu Thr Gln Ser Thr Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Gly Gly Thr Lys Leu Glu Ile Lys
            100                 105                 110

<210> SEQ ID NO 64
<211> LENGTH: 117
<212> TYPE: PRT
<213> ORGANISM: Mus musculus

<400> SEQUENCE: 64

Glu Val Gln Leu Gln Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Gly Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Gly Asp Val Glu Phe Asp Tyr Trp Gly Gly Thr Thr
            100                 105                 110

Leu Thr Val Ser Ser
        115

<210> SEQ ID NO 65
<211> LENGTH: 107
<212> TYPE: PRT
<213> ORGANISM: Mus musculus

<400> SEQUENCE: 65

Gln Ile Val Leu Thr Gln Ser Pro Thr Ile Met Ser Ala Ser Pro Gly
1               5                   10                  15

Glu Lys Val Thr Ile Ser Cys Ser Ala Ser Ser Ser Val Ser Tyr Met
```

```
                   20                  25                  30

Tyr Trp Tyr Gln Gln Lys Pro Gly Ser Ser Pro Lys Pro Trp Ile Tyr
            35                  40                  45

Arg Thr Ser Asn Leu Ala Ser Gly Val Pro Asp Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Arg Thr
                85                  90                  95

Phe Gly Gly Gly Thr Lys Leu Glu Ile Lys Arg
            100                 105

<210> SEQ ID NO 66
<211> LENGTH: 118
<212> TYPE: PRT
<213> ORGANISM: Mus musculus

<400> SEQUENCE: 66

Val Gln Leu Gln Gln Ser Gly Ala Glu Leu Ala Arg Pro Gly Ala Ser
1               5                   10                  15

Val Lys Leu Ser Cys Lys Ala Ser Gly Tyr Thr Phe Thr Thr Tyr Gly
            20                  25                  30

Leu Thr Trp Val Lys Gln Arg Thr Gly Gln Gly Leu Glu Trp Ile Gly
        35                  40                  45

Glu Ile Phe Pro Gly Ser Gly Thr Thr Phe Tyr Asn Glu Lys Phe Asn
    50                  55                  60

Asp Lys Ala Thr Leu Thr Ala Asp Lys Ser Ser Ser Thr Ala Tyr Met
65                  70                  75                  80

Gln Leu Thr Ser Leu Thr Ser Glu Asp Ser Ala Val Tyr Phe Cys Ala
                85                  90                  95

Arg Tyr Ser Asn Tyr Pro Tyr Tyr Phe Asp Tyr Trp Gly Gln Gly Thr
            100                 105                 110

Thr Leu Thr Val Ser Ser
        115

<210> SEQ ID NO 67
<211> LENGTH: 336
<212> TYPE: DNA
<213> ORGANISM: Mus musculus

<400> SEQUENCE: 67
attgtgctga cacagactac atcctccctg gctgtgtcag caggagagaa ggtcactatg      60
agctgcaaat ccagtcagag tctgctcaac agtagaaccc aaagaactac ttggcttgg     120 taccagcaga aaccagggca gtctcctaaa ctgctgatct actgggcatc cactaggaaa    180
tctggggtcc ctgatcgctt cacaggcagt ggatctggga cagatttcac tctcaccatc    240
agcagtgtgc aggctgaaga cctggcagtt tattactgca gcaatcttta taatctgctc    300
acgttcggtg ctgggaccaa gctggagctg aaacgg                              336

<210> SEQ ID NO 68
<211> LENGTH: 357
<212> TYPE: DNA
<213> ORGANISM: Mus musculus

<400> SEQUENCE: 68
gtccagctgg aggagtcagg ggctgaactg gtgaagcctg ggcttcagt gaaattgtcc       60
```

| | |
|---|---:|
| tgcaaggctt ctggctacgc cttcacccac tactatatat actggataaa acagaggcct | 120 |
| ggacaaggcc ttgagtggat tgggggggtt aatcctagca atggtggtac tcacttcaat | 180 |
| gagaagttca agagcaaggc cacactgact gtagacaaat cctccagtac agcctacatg | 240 |
| caactcagca gcctgacatc tgaggactct gcggtctatt attgtacaag atcggagtat | 300 |
| gattacggat tggggtttgc ttactggggc caagggactc tggtcactgt ctctgca | 357 |

<210> SEQ ID NO 69
<211> LENGTH: 339
<212> TYPE: DNA
<213> ORGANISM: Mus musculus

<400> SEQUENCE: 69

| | |
|---|---:|
| gacattgtga tcacacagtc tccatcctcc ctggctgtgt cagcaggaga gaaggtcact | 60 |
| atgagctgca gatccagtca gagtctgctc gacagtagaa cccgaaagaa ctacttggct | 120 |
| tggtaccagc agaaaccagg gcagtctcct aaactgctga tctactgggc atccactagg | 180 |
| gaatctgggg tccctgatcg cttcacaggc agtggatctg gacagatttc actctcacc | 240 |
| atcagcaatg tgcaggctga agacctggca gtttattact gcaagcaatc ttataatctt | 300 |
| ccgacgttcg gtggaggcac caagctggaa atcaaacgg | 339 |

<210> SEQ ID NO 70
<211> LENGTH: 348
<212> TYPE: DNA
<213> ORGANISM: Mus musculus

<400> SEQUENCE: 70

| | |
|---|---:|
| gttaagctgc aggagtcagg aggaggcttg gtgcaacctg gaggcccat gaaactctcc | 60 |
| tgtgttgcct ctggattcac ttttagtgac ttctggatga actgggtccg ccagtctcca | 120 |
| gagaaaggac tggagtgggt agcacaaatt agaaacaaac taataatta tgaaacgtat | 180 |
| tattcagatt ctttgaaagg cagattcacc atctcaagag atgattccaa agtagtgtc | 240 |
| tacctgcaaa tgaacaactt aagacctgaa gacatgggta tctattactg tacactaggt | 300 |
| aactcctggt ttgcttactg gggccaaggg actctggtca ctgtctct | 348 |

<210> SEQ ID NO 71
<211> LENGTH: 318
<212> TYPE: DNA
<213> ORGANISM: Mus musculus

<400> SEQUENCE: 71

| | |
|---|---:|
| caaattgttc tcacccagtc tccagcaatc atgtctgcat ctccagggga gaaggtcacc | 60 |
| atgacctgca gtgccagctc aagtgtaagt tacatgtatt ggtaccagca gaagtcaggc | 120 |
| acctccccca aaagatggat ttatgacaca tccaaactgg cttctggagt ccctgctcgt | 180 |
| ttcagtggca gtgggtctgg gacctcttac tctctcacaa tcagcagcat ggaggctgaa | 240 |
| gatgctgcca cttattactg ccagcagtgg agtagtaacc cacagttcgg tactgggacc | 300 |
| aagctggagg tgaaacgg | 318 |

<210> SEQ ID NO 72
<211> LENGTH: 357
<212> TYPE: DNA
<213> ORGANISM: Mus musculus

<400> SEQUENCE: 72

| | |
|---|---:|
| caggtaaagc tggaggagtc aggacctgag ctggtgaagc ctggggctcc agtgaagata | 60 |

```
tcctgcaaga cttctggcta caccttcact aactactata tatattgggt gaaacagagg    120
cctggacagg gcctagagtg gattggatat atttatcctg gaaatggtgg tactgcctac    180
aatcagaaat ttaaggacaa ggccacactg actgcagaca atccctccaa cactgcctac    240
atgcagctca gtagcctgac ctctgaggac tctgcggtct atctctgtgc aagaagaggg    300
gctttaggat actactttga ctactggggc caaggcacca ctctcacagt ctcctca      357
```

<210> SEQ ID NO 73
<211> LENGTH: 321
<212> TYPE: DNA
<213> ORGANISM: Mus musculus

<400> SEQUENCE: 73

```
caaattgttc tcacccagtc tccagcaatc atgtctgcat ctccagggga gaaggtcacc     60
atgacctgca gtgccagctc aagtgtaact tacatgcact ggtaccagca gaagtcaggc    120 acctcccca aaagatggat ttatgacaca tccaaactgg cttctggagt ccctgctcgc    180
ttcagtggca gtgggtctgg gacctcttac tctctcacaa tcagcaccat ggaggctgaa    240
gatgctgcca cttattactg ccagcagtgg attagtaacc cacccacgtt cggagggggg    300
accaagctgg aaataaaacg g                                              321
```

<210> SEQ ID NO 74
<211> LENGTH: 348
<212> TYPE: DNA
<213> ORGANISM: Mus musculus

<400> SEQUENCE: 74

```
caggttcagc tgcagcagtc tggagctgag ctggcgaggc ctggggcttc agtgaagctg     60
tcctgcaagg cttctggata ttccctcaca aactatggta aagttgggt gaagcagaga    120 actggacagg gccttgagtg gattggagag atttatcgtg gaagtggtaa tagttactac    180
aatgagaagt tcaagggcaa ggcctcactg actgcagaca atcctccag cacagcctac    240 atgcagctca gcagcctgac atctgaggac tctgccgtct atttctgtgc aagagggggg    300
ctatcctttg cttactgggg ccaagggact ctggtcactg tctctgca                 348
```

<210> SEQ ID NO 75
<211> LENGTH: 324
<212> TYPE: DNA
<213> ORGANISM: Mus musculus

<400> SEQUENCE: 75

```
gatattgtga tgacccagtc tacagcctcc ctatctgcat ctgtgggaga aactgtcacc     60
atcacatgtc gagcaagtga gaatatttac acttatttag catggtatca gcagaaacag    120
ggaaaatctc ctcagctcct ggtctataat gcaaaaacct agcagaagg tgtgccatca    180 aggttcagtg gcagtggatc aggcacacag ttttctctga ggatcaacag cctgcagcct    240
gaagattttg ggagttatta ctgtcaacat cattatggta ccccgtacac gttcggaggg    300
gggaccaagc tggaaataaa acgg                                           324
```

<210> SEQ ID NO 76
<211> LENGTH: 360
<212> TYPE: DNA
<213> ORGANISM: Mus musculus

<400> SEQUENCE: 76

```
caggtcaagc tgcaggagtc aggagctgag ctgatgaagc ctgggtcctc agtgaagttt      60
tcctgcaagg ctgctggcta cacattcact gactattgga tagagtggtt aaagcagagg     120
cctggacatg gccttgagtg gattggagag attttacctg gaagtgttag tattaagtac     180
aatgagaagt tcaagggcaa ggccacattc actgcagata catcctccaa cacagcctac     240
atgcaactca gcagcctgac atctgaggat tctgcggtct attactgtgc aagatcaagg     300
tctatctatg atggttactt ttattactgg ggccaaggca ccactctcac agtctcctca     360
```

<210> SEQ ID NO 77
<211> LENGTH: 321
<212> TYPE: DNA
<213> ORGANISM: Mus musculus

<400> SEQUENCE: 77

```
gatattgtga tgacacagtc tccagcaatc atgtctgcat ctcctgggga aaggtcacc      60 atttcctgca gtgccagctc aagtgtaagt tacatgtact ggtaccagca gaagccagga    120
tcctccccca aaccctggat ttatcgcaca tccaacctgg cttctggagt ccctgctcgc    180
ttcagtggca gtgggtctgg gacctcttac tctctcacaa tcagcagcat ggaggctgaa    240
gatgctgcca cttattactg ccagcagtat catagttacc cacggacgtt cggtggaggc    300
accaagctgg aaatcaaacg g                                              321
```

<210> SEQ ID NO 78
<211> LENGTH: 357
<212> TYPE: DNA
<213> ORGANISM: Mus musculus

<400> SEQUENCE: 78

```
gaggtgcagc tgcaggagtc tggagctgag ctggcgaggc ctggggcttc agtgaagctg     60
tcctgcaagg cttctggata cagcttcaga agctatggta taaactgggt gaagcagaga    120
actggacagg gccttgagtg gattggagag atttatcctg aagtggtac tactttctac    180 aatgagaagt tcaggggcaa ggccacactg actgcagaca gtcctccag cacagcctac    240 atgcagctca aaagcctgac atctgaggac tctgccgtct atttctgtgc aagacatggt    300
ggttacccgt tctactttga ctactgggc caaggcacca ctctcacagt ctcctca       357
```

<210> SEQ ID NO 79
<211> LENGTH: 336
<212> TYPE: DNA
<213> ORGANISM: Mus musculus

<400> SEQUENCE: 79

```
gatattgtgc tgacccaatc tacagcttct ttggctgtgt ctctagggca gagggccacc     60
atatcctgca gagccagtga agtgttgat agttatggca atagttttat gcactggtac    120
cagcagaaac caggacagcc acccaaactc ctcatctatc gtgcatccaa cctagaatct    180
gggatccctg ccaggttcag tggcagtggg tctaggacag acttcaccct caccattaat    240
cctgtggagg ctgatgatgt tgcaacctac tactgtcagc aaagtaatga ggatcctccc    300
acgttcggct cggggacaaa gttggaaata aaacgg                             336
```

<210> SEQ ID NO 80
<211> LENGTH: 351
<212> TYPE: DNA
<213> ORGANISM: Mus musculus

<400> SEQUENCE: 80

```
gaagtgcagc tgcaggagtc aggccctggg atattgcagc cctcccagac cctcagtctg    60
acttgttctt tctctgggtt ttcactgagc acttctggta tgggtgtgag ctggattcgt   120
cagccttcag gaaagggtct ggagtggctg gcacacattt actgggatga tgacaagggc   180
tataacccat ccctgaagag ccggctcaca atctccaagg atacctccag aaaccaggta   240
ttcctcaaga tcaccagtgt ggacactgca gatactgcca catactactg tgctcgaggg   300
gacgtcgagt ttgactactg gggccaaggc accactctca cagtctcctc a            351
```

<210> SEQ ID NO 81
<211> LENGTH: 321
<212> TYPE: DNA
<213> ORGANISM: Mus musculus

<400> SEQUENCE: 81

```
caaattgttc tcacccagtc tccaacaatc atgtctgcat ctccagggga agaggtcacc    60
atatcctgca gtgccagctc aagtgtaagt tacatgtact ggtaccagca gaagccagga   120
tcctccccca aaccctggat ttatcgcaca tccaacctgg cttctggagt ccctgatcgc   180
ttcagtggca gtgggtctgg gacctcttac tctctcacaa tcagcagcat ggaggctgaa   240
gatgctgcca cttattactg ccagcagtat catagttacc cacggacgtt cggtggaggc   300
accaagctgg aaatcaaacg g                                             321
```

<210> SEQ ID NO 82
<211> LENGTH: 357
<212> TYPE: DNA
<213> ORGANISM: Mus musculus

<400> SEQUENCE: 82

```
gaagtgcagc tgcagcagtc aggagctgaa ctggcgaggc ctggggcttc agtgaagctg    60
tcctgcaagg cttctggata caccttcaca acctatggtt taacctgggt gaagcagaga   120
actggacagg gccttgagtg gattggagag atttttcctg gaagtggtac tactttctac   180
aatgagaagt tcaacgacaa ggccacactg actgcagaca atcctccag cacagcctac   240 atgcagctca ccagcctgac atctgaggac tctgccgtct atttctgtgc aagatatagt   300
aactacccgt actactttga ctactggggc caaggcacca ctctcacagt ctcctca      357
```

<210> SEQ ID NO 83
<211> LENGTH: 10
<212> TYPE: PRT
<213> ORGANISM: Homo sapiens

<400> SEQUENCE: 83

Lys Pro Leu Pro Glu Val Thr Asp Glu Tyr
1               5                   10

<210> SEQ ID NO 84
<211> LENGTH: 18
<212> TYPE: PRT
<213> ORGANISM: Homo sapiens

<400> SEQUENCE: 84

Glu Lys Glu Ala Leu Lys Lys Ile Ile Glu Asp Gln Gln Glu Ser Leu
1               5                   10                  15

Asn Lys

<210> SEQ ID NO 85

```
<211> LENGTH: 18
<212> TYPE: PRT
<213> ORGANISM: Artificial
<220> FEATURE:
<223> OTHER INFORMATION: Linker peptide

<400> SEQUENCE: 85

Glu Lys Glu Ala Leu Lys Lys Ile Ile Glu Asp Gln Gln Glu Ser Leu
1               5                   10                  15

Asn Lys

<210> SEQ ID NO 86
<211> LENGTH: 50
<212> TYPE: PRT
<213> ORGANISM: Homo sapiens

<400> SEQUENCE: 86

Val Thr Trp Glu Val Leu Glu Gly Glu Val Glu Lys Glu Ala Leu Lys
1               5                   10                  15

Lys Ile Ile Glu Asp Gln Gln Glu Ser Leu Asn Lys Trp Lys Ser Lys
                20                  25                  30

Gly Arg Arg Phe Lys Gly Lys Gly Lys Gly Asn Lys Ala Ala Gln Pro
            35                  40                  45

Gly Ser
    50

<210> SEQ ID NO 87
<211> LENGTH: 42
<212> TYPE: PRT
<213> ORGANISM: Homo sapiens

<400> SEQUENCE: 87

Trp Glu Val Leu Glu Gly Glu Val Glu Lys Glu Ala Leu Lys Lys Ile
1               5                   10                  15

Ile Glu Asp Gln Gln Glu Ser Leu Asn Lys Trp Lys Ser Lys Gly Arg
                20                  25                  30

Arg Phe Lys Gly Lys Gly Lys Gly Asn Lys
            35                  40

<210> SEQ ID NO 88
<211> LENGTH: 36
<212> TYPE: PRT
<213> ORGANISM: Homo sapiens

<400> SEQUENCE: 88

Trp Glu Val Leu Glu Gly Glu Val Glu Lys Glu Ala Leu Lys Lys Ile
1               5                   10                  15

Ile Glu Asp Gln Gln Glu Ser Leu Asn Lys Trp Lys Ser Lys Gly Arg
                20                  25                  30

Arg Phe Lys Gly
            35

<210> SEQ ID NO 89
<211> LENGTH: 31
<212> TYPE: PRT
<213> ORGANISM: Homo sapiens

<400> SEQUENCE: 89

Trp Glu Val Leu Glu Gly Glu Val Glu Lys Glu Ala Leu Lys Lys Ile
1               5                   10                  15

Ile Glu Asp Gln Gln Glu Ser Leu Asn Lys Trp Lys Ser Lys Gly
```

```
<210> SEQ ID NO 90
<211> LENGTH: 29
<212> TYPE: PRT
<213> ORGANISM: Homo sapiens

<400> SEQUENCE: 90

Trp Glu Val Leu Glu Gly Glu Val Lys Glu Ala Leu Lys Lys Ile
1               5                   10                  15

Ile Glu Asp Gln Gln Glu Ser Leu Asn Lys Trp Lys Ser
                20                  25

<210> SEQ ID NO 91
<211> LENGTH: 24
<212> TYPE: PRT
<213> ORGANISM: Homo sapiens

<400> SEQUENCE: 91

Leu Glu Gly Glu Val Lys Glu Ala Leu Lys Lys Ile Ile Glu Asp
1               5                   10                  15

Gln Gln Glu Ser Leu Asn Lys Trp
                20

<210> SEQ ID NO 92
<211> LENGTH: 25
<212> TYPE: PRT
<213> ORGANISM: Homo sapiens

<400> SEQUENCE: 92

Glu Val Glu Lys Glu Ala Leu Lys Lys Ile Ile Glu Asp Gln Gln Glu
1               5                   10                  15

Ser Leu Asn Lys Trp Lys Ser Lys Gly
                20                  25

<210> SEQ ID NO 93
<211> LENGTH: 21
<212> TYPE: PRT
<213> ORGANISM: Homo sapiens

<400> SEQUENCE: 93

Glu Val Glu Lys Glu Ala Leu Lys Lys Ile Ile Glu Asp Gln Gln Glu
1               5                   10                  15

Ser Leu Asn Lys Trp
                20

<210> SEQ ID NO 94
<211> LENGTH: 15
<212> TYPE: PRT
<213> ORGANISM: Homo sapiens

<400> SEQUENCE: 94

Glu Val Glu Lys Glu Ala Leu Lys Lys Ile Ile Glu Asp Gln Gln
1               5                   10                  15

<210> SEQ ID NO 95
<211> LENGTH: 21
<212> TYPE: PRT
<213> ORGANISM: Homo sapiens

<400> SEQUENCE: 95

Glu Lys Glu Ala Leu Lys Lys Ile Ile Glu Asp Gln Gln Glu Ser Leu
1               5                   10                  15
```

```
Asn Lys Trp Lys Ser
            20

<210> SEQ ID NO 96
<211> LENGTH: 18
<212> TYPE: PRT
<213> ORGANISM: Homo sapiens

<400> SEQUENCE: 96

Glu Lys Glu Ala Leu Lys Lys Ile Ile Glu Asp Gln Gln Glu Ser Leu
1               5                   10                  15

Asn Lys

<210> SEQ ID NO 97
<211> LENGTH: 17
<212> TYPE: PRT
<213> ORGANISM: Homo sapiens

<400> SEQUENCE: 97

Glu Lys Glu Ala Leu Lys Lys Ile Ile Glu Asp Gln Gln Glu Ser Leu
1               5                   10                  15

Asn

<210> SEQ ID NO 98
<211> LENGTH: 16
<212> TYPE: PRT
<213> ORGANISM: Homo sapiens

<400> SEQUENCE: 98

Glu Ala Leu Lys Lys Ile Ile Glu Asp Gln Gln Glu Ser Leu Asn Lys
1               5                   10                  15
```

ANTI-LA ANTIBODIES AND THEIR USE FOR IMMUNOTARGETING

CROSS-REFERENCE TO RELATED APPLICATIONS

This application is a divisional of U.S. patent application Ser. No. 13/814,510, filed May 3, 2013, which is a U.S. National Phase filing under 35 U.S.C. § 371 of International Application No. PCT/EP2011/063539, filed Aug. 5, 2011, which claims benefit of priority to German Patent Application No. 10 2010 039 018.6, filed Aug. 6, 2010, the entire disclosures of which are hereby incorporated by reference herein.

BACKGROUND OF THE INVENTION

The invention concerns antibodies against the human La protein and their use for immunotargeting, in particular of tumor cells. The antibodies according to the invention are suited for use in the field of medicine, pharmacy and in biomedical research.

The human La protein (hLa) was originally disclosed as an auto-antigen in patients with systemic lupus erythematosus (SLE, Mattioli, M., Reichlin, M., 1974. Arthritis & Rheumatism; 17 (4): 421-29) and Sjögren syndrome (Alspaugh, M. A., Tan, E. M., 1975. J Clin Invest; 55 (5): 1067-73) and is known by the alternative name SS-B (Sjögren syndrome antigen B).

With $2 \cdot 10^7$ molecules per human cell it is an abundant protein which is found in all tissues. La has a functional role in RNA metabolism and as a RNA chaperon, it processes pre-tRNA precursor molecules and influences the exactness as well as the efficiency of the RNA polymerase III transcription in vitro (inter alia Gottlieb, E. et al., 1989 EMBO J; 8 (3): 841-50).

Chambers et al. (1988. *J Biol. Chem.*, 263, 18043-18051) determined the amino acid sequence of La protein and 3 antigen epitope regions and made predictions about the regions which are involved in RNA binding.

The primary structure of hLa protein (FIG. 1A; SEQ ID No. 1) can be divided into three regions which form spatial domains that are independent of each other (see FIG. 1B). The La motif is N-terminal, followed by central RNA recognition motif (RNA recognition motif, RRM) which is also referred to as RRM1. These two domains form the N-terminal half of the protein and together referred to as LaN. The second half, LaC, contains the C-terminal RRM (RRM2) as well as an adjoining long, flexible element of about 80 AS that exhibits no secondary structure characteristics. According to Chambers et al. (1988), the N-terminal RRM1 is particularly immunogenic.

McNeilage et al. (1984. *J. Clin. Rennet. Immunol.* 15, 1-17, *Clin. exp. Immunol.*, 1985, 62, 685-695) examine anti La antibodies formed by patients with autoimmune illnesses and which RNA and protein components are recognized by these antibodies. Scofield R H et al. examined the fine specificity of the autoimmune response against the Ro/SSA and La/SSB ribonucleoproteins (1999, Arthritis Rheum. 42 (2):199-209).

Chan E K et al. (1987 J Exp Med 166 (6):1627-40) compare La epitopes which are recognized by human auto-antibodies and mouse antibodies against human and bovine La. For this purpose, 5 monoclonal mouse antibodies were produced which were obtained by immunization of mice with bovine La. A cross-reactivity of the mouse antibodies with murine La protein was not found.

Bachmann et al. (1990. *Exp. Cell Res.* 191, 171-180. 1991. *Autoimmunity* 9, 99-107. 1992 *Autoimmunity* 12, 37-45) describe that the auto-antigen La reaches the cell surface in UV-irradiated keranocytes and cells infected with herpes simplex type 1.

U.S. Pat. No. 5,457,029 describes a diagnostic test for detecting anti-La antibodies.

U.S. Pat. No. 4,751,181 discloses a procedure for producing the La protein antigen.

U.S. Pat. No. 4,784,942 discloses a murine anti-La antibody (hybridoma LA1, ATCC: HB-8609) which was obtained by immunization with bovine La protein.

Smith P R et al. (1985 J Immunol Methods 77(1):63-76) describe a murine anti-La antibody (SW5) which was obtained from rabbit by immunization with La protein.

Human monoclonal La antibodies were disclosed by Mamula M J (1989 J Immunol 143 (9):2923-8).

Offen D et al. (1990 J Autoimmune. 3 (6):701-13) describe murine anti-La antibodies directed against an ideo-type (16/6 Id) spread in SLE patients.

In the following, the antibodies against the human La protein that are known in the art are summarized:

La1B5 Bachmann et al. PNAS USA vol. 83: 7770-7774, 1986;

8G3 and 9A5 Mamula et al. J Immunol 143 (9):2923-2928, 1989;

anti-human La Carmo-Fonseca et al. ExpCellRes 185(1): 73-85, 1989;

4B6 Tröster et al. J Autoimmunity 8 (6): 825-842, 1995;

SW1, SW3, SW5 Smith P R et al. J Immunol Methods. 77(1): 63-76, 1985; Pruijn et al. Eur J Biochem 232: 611-619, 1995;

3B9 Tran et al. Arthritis Rheum 46(1): 202-208, 2002;

DAB4 Al Ej eh et al. Nucl Med Biol. 2009, 36(4): 395-402.

All of these antibodies are monoclonal antibodies which bind to the human La protein. The CDR sequences of these antibodies are unknown except for SW5.

4B6 binds the La epitope with the sequence SKGRRFK-GKGKGN (AS 330-343 of the human La protein, SEQ ID No. 2).

Al-Ej eh F. et al. (2007. Clin Cancer Res. 13 (18 Pt 2):55095-5518s) describe that the La protein is expressed at increased levels in tumor cells. It was found that, with increasing DNA damage, the anti-La antibody 3B9 binds increasingly to tumor cells. It is described that the La antigen is cross-linked in dead malignant cells by transglutaminase 2. Based on this, Al-Ejeh F et al. (2007. Clin Cancer Res. 13 (18 Pt 2):55195-5527s) describe in a mouse model the use of anti-La 3B9 for in vivo targeting of tumor cells. Targeting was further improved by concurrent cytostatic treatment. Al-Ejeh F et al. (2009. PLoS One. 4 (2):e4630) describe a radio immunotherapy in which tumor targeting is done with the monoclonal anti-La antibody DAB4. The radio immunotherapy is carried out in combination with chemotherapy. WO 2008/043148 A1 discloses also combination therapy of anti-La antibodies with cytostatic agents.

In Al-Ejeh F et al. (2009. PLoS One. 2009; 4 (2):e4558) the use of the anti-La antibody DAB4 is described for the detection of the tumor response to DNA-damaging chemotherapeutic agents.

A general problem of the therapeutic effectiveness of monoclonal antibodies in tumor treatment is the binding capacity of the antibodies to the cancer cells, i.e., the affinity of the antibodies and the selection of the suitable antigen which is bound by the antibodies. Specific tumor antigens mostly are not expressed in sufficient amounts on the cancer cells. In cancer cells that sufficiently express tumor antigens, the binding rate of the used antibodies is often not high enough. Moreover, with a molecular mass of about 150 kDa antibodies are limited in general with regard to tissue mobility. In this case, antibody fragments, like Fab, F(ab)$_2$ or scFv (single chain variable fragments), on account of their clearly smaller size, have considerable advantages.

Bispecific antibodies, i.e., antibody derivatives of components of two different monoclonal antibodies, offer new possibilities for therapy concepts in cancer immunotherapy. US 2005/0136050 A1 discloses bispecific antibodies which can bind to two different targets. They serve for recruiting human immune effector cells to a target antigen which is located on a target cell.

Quadromas are bispecific antibodies of the first generation and are comprised of a heavy chain and a light chain of two different monoclonal antibodies. The two arms of the antibody are each directed against different antigens. The Fc part is formed jointly of both heavy chains of the antibodies. With this construction it is, for example, possible to position the paratope of an antibody directed against a tumor antigen and the paratope of a further antibody directed against a lymphocyte antigen onto one arm of the bispecific antibody, respectively. It is so possible to form a three-cell complex resulting from the cells bound in each case by the different paratopes and the effector cell bound by the Fc part. In this context, an improved activation of the body's own immune cells arises generally relative to the tumor cells.

Bispecific antibodies of the newer generation are constructed of two different scFv fragments. These are connected to each other by a linker peptide. Thus, a bispecific antibody can bind, for example, with one scFv to tumor cells and with the other scFv to effector cells.

When a paratope is directed against T cells, these cells can be also activated. With normal monoclonal antibodies this is not possible because T cells do not have Fc receptors. In addition, bispecific antibodies have a higher cytotoxic potential. They also bind to antigens which are expressed relatively weakly.

To this day, no bispecific antibodies have been approved for clinical use in humans.

Bispecific antibodies are known where an scFv binds to the CD3 complex on T cells, these are also called BiTE (bispecific T cell engager) (P. A. Baeuerle et. al., BiTE: Teaching antibodies to engage T cells for cancer therapy. Curr Opin Mol Ther 11, 2009, pages 22-30).

At the moment, two different BiTE antibodies are in clinical studies. Blinatumomab, an antibody directed against CD3 and CD19, is tested in patients in late phases of Non-Hodgkin lymphoma and in patients with acute lymphoblastic leukemia of the B cell line (B-ALL). MT110 is an antibody which is directed against CD3 and EpCAM (epithelial cell adhesion molecule) and is tested in patients with bronchial carcinoma and patients with gastrointestinal cancer diseases (R. Bargou en. al., Tumor regression in cancer patients by very low doses of a T cell-engaging antibody. Science 321, 2008, pages 974-977; K. Brischwein et al., MT110: a novel bispecific single chain antibody construct with high efficacy in eradicating established tumors. Mol Immunol 43, 2006, pages 1129-1143).

Not all monoclonal antibodies are suitable in the form of scFv fragments or for the construction of bispecific constructs. Particularly the affinity of the antibodies is decisive which is determined by the variable regions. Only particularly high-affinity antibodies are suited as scFv fragments because binding occurs at the respective antigen only with one pair of variable regions of the heavy and light chains, in contrast to the complete IgG antibodies which have two pairs of variable regions of the heavy and light chains.

For the treatment of carcinomas there is a need for new therapeutic concepts.

A big problem with immuno-targeting of cells, in particular in immunotherapy of tumors, is either the absence of specific targets or the loss of a specific target in some of the tumor cells. Therefore, no suitable targeting module could be developed up to now for many target cells.

The object of the invention is providing improved antibodies which bind universal target structures on the surface of tumor cells.

SUMMARY OF THE INVENTION

The invention is based on the finding that the nuclear antigen La is released by injured or dying cells and can bind to neighboring intact cells where it is stable for more than 24 hrs. on their surface and is accessible to the antibody. By antibody binding even NK cells can be activated and thus cause an antibody-induced destruction (ADCC) of the intact cells.

In the context of tumor therapy (for example, with cytostatic agents or radiation therapy), the nuclear antigen La is released by apoptotic tumor cells and binds to the surface of neighboring tumor cells. Therefore, the La protein represents an inducible universal surface target (a universal target structure on the surface of the tumor cells).

The goal of the invention was therefore to develop antibodies or recombinant antibody derivatives which allow to recognize target cells (in particular tumor cells) and to activate immune effector cells (e.g., T cells, NK cells, dendritic cells) against them.

Another object of the invention is therefore providing new anti-La antibodies, in particular with a high affinity to La which enable the use of the antibodies as recombinant fragments for immuno-targeting.

The object is solved according to the invention by new anti-La antibodies as well as recombinant antibodies which contain regions determining complementarity (complementary determining regions, CDRs) which are characterized in that the CDRs of the variable region of the light chain ($V_L$—left column) and the CDRs of the variable region of the heavy chain ($V_H$—right column) comprise the sequences disclosed in one of the Tables 1 to 8:

TABLE 1

| Antibody 5B9: | | | |
|---|---|---|---|
| $V_L$ | SEQ ID No. | $V_H$ | SEQ ID No. |
| CDR1 KSSQSLLNSRTPKNYLA | 3 | HYYIY | 4 |
| CDR2 WASTRKS | 5 | GVNPSNGGTHFNEKFKS | 6 |
| CDR3 KQSYNLLT | 7 | SEYDYGLGFAY | 8 |

TABLE 2

Antibody 7B6:

| | V<sub>L</sub> | SEQ ID No. | V<sub>H</sub> | SEQ ID No. |
|---|---|---|---|---|
| CDR1 | RSSQSLLDSRTRKNYLA | 9 | DFWMN | 10 |
| CDR2 | WASTRES | 11 | QIRNKPNNYETYYSDSLKG | 12 |
| CDR3 | KQSYNLPT | 13 | LGNSWFAY | 14 |

TABLE 3

Antibody 22A:

| | V$_L$ | SEQ ID No. | V$_H$ | SEQ ID No. |
|---|---|---|---|---|
| CDR1 | SASSSVSYMY | 15 | NYYIY | 16 |
| CDR2 | DTSKLAS | 17 | YIYPGNGGTAYNQKFKD | 18 |
| CDR3 | QQWSSNPQ | 19 | RGALGYYFDY | 20 |

TABLE 4

Antibody 24BG7:

| | V$_L$ | SEQ ID No. | V$_H$ | SEQ ID No. |
|---|---|---|---|---|
| CDR1 | SASSSVTYMEI | 21 | NYGIS | 22 |
| CDR2 | DTSKLAS | 23 | EIYRGSGNSYYNEKFKG | 24 |
| CDR3 | QQWISNPPT | 25 | GGLSFAY | 26 |

TABLE 5

Antibody 312B:

| | V$_L$ | SEQ ID No. | V$_H$ | SEQ ID No. |
|---|---|---|---|---|
| CDR1 | RASENIYTYLA | 27 | DYWIE | 28 |
| CDR2 | NAKTLAE | 29 | EILPGSVSIKYNEKFKG | 30 |
| CDR3 | QHHYGTPYT | 31 | SRSIYDGYFYY | 32 |

TABLE 6

Antibody 27E:

| | V$_L$ | SEQ ID No. | V$_H$ | SEQ ID No. |
|---|---|---|---|---|
| CDR1 | SASSSVSYMY | 33 | SYGIN | 34 |
| CDR2 | RTSNLAS | 35 | EIYPGSGTTFYNEKFRG | 36 |
| CDR3 | QQYHSYPRT | 37 | HGGYPFYFDY | 38 |

TABLE 7

Antibody 2F9:

| | V$_L$ | SEQ ID No. | V$_H$ | SEQ ID No. |
|---|---|---|---|---|
| CDR1 | RASESVDSYGNSFMH | 39 | TSGMGVS | 40 |
| CDR2 | RASNLES | 41 | HIYWDDDKGYNPSLKS | 42 |
| CDR3 | QQSNEDPPT | 43 | GDVEFDY | 44 |

TABLE 8

Antibody 32A

| | V$_L$ | SEQ ID No. | V$_H$ | SEQ ID No. |
|---|---|---|---|---|
| CDR1 | SASSSVSYMY | 45 | TYGLT | 46 |
| CDR2 | RTSNLAS | 47 | EIFPGSGTTFYNEKFND | 48 |
| CDR3 | QQYHSYPRT | 49 | YSNYPYYFDY | 50 |

The antibodies comprise preferably the following, optionally humanized, variable regions of the light chains (V$_L$) and/or heavy chains (V$_H$):

TABLE 9

| Antibody | V$_L$ SEQ ID No. | V$_H$ SEQ ID No. |
|---|---|---|
| 5B9 | 51 | 52 |
| 7B6 | 53 | 54 |
| 22A | 55 | 56 |
| 24BG7 | 57 | 58 |
| 312B | 59 | 60 |
| 27E | 61 | 62 |
| 2F9 | 63 | 64 |
| 32A | 65 | 66 |

The anti-La antibody according to the invention, herein also referred to as "anti-La", are characterized by their CDRs and preferably the aforementioned amino acid sequences of the variable regions of the heavy and the light chains.

Subject matter of the invention are also gene sequences which code for the aforementioned amino acid sequences of the variable regions of the light chains (V$_L$) and/or heavy chains on (V$_H$):

TABLE 10

| Antibody | V$_L$-DNA SEQ ID No. | V$_H$-DNA SEQ ID No. |
|---|---|---|
| 5B9 | 67 | 68 |
| 7B6 | 69 | 70 |
| 22A | 71 | 72 |
| 24BG7 | 73 | 74 |
| 312B | 75 | 76 |
| 27E | 77 | 76 |
| 2F9 | 79 | 80 |
| 32A | 81 | 82 |

Advantageously, the anti-La antibodies according to the invention can still bind the La epitope even when the nuclear antigen is present bound to the surface of cells. In a cell culture model it has been demonstrated that the anti-La antibodies according to the invention bind to La protein bound to the cell surface and the cells are killed by NK cells in an antibody-dependent cell-induced cytotoxicity (antibody dependent cellular cytotoxicity—ADCC).

The epitopes recognized by the antibodies according to the invention on the human La protein are summarized in the following Table 11:

TABLE 11

| Antibody | Structure of the epitope | epitopes (AS of hLa) | Redox dependency |
|---|---|---|---|
| 5B9 | linear, SEQ ID No. 83 | 95-104 | (−) |
| 7B6 | linear, SEQ ID No. 84 | 311-328 | (+) oxidized |
| 22A | conformation | 107-200 | (−) |
| 24BG7 | conformation | 107-200 | (−) |
| 312B | conformation | 10-100 | (+) reduced |
| 27E | conformation | 10-100 | (+) reduced |
| 2F9 | conformation | 10-100 | (+) reduced |
| 32A | conformation | 10-100 | (+) reduced |

Particularly preferred is the antibody 7B6 or an antibody with the aforementioned CDRs of the variable regions of the light chains ($V_L$) and heavy chains ($V_H$) (SEQ ID Nos. 9 to 14) and preferably the variable regions of the light chains ($V_L$) and/or heavy chains (VH) according to SEQ ID Nos. 53 and 54 or corresponding humanized structures. Advantageously, this antibody binds a redox-dependent epitope which becomes accessible under oxidative conditions in the La protein. Such oxidative conditions ("oxidative stress") exist in tumor tissue, in particular as a reaction to radiation and/or chemotherapy (in particular cytostatic agent therapy). Oxidative stress refers to a metabolism situation in which reactive oxygen compounds (ROS—reactive oxygen species) are formed. The fact that the 7B6 epitope under these oxidative conditions becomes accessible in La enables a more specific anti-tumor therapy with reduced side effects. La which is released in other tissue (non-tumor tissue) by dying cells under non-oxidative conditions is not bound by this antibody. The epitope of 7B6 is made accessible only by oxidative stress. Otherwise, the epitope is cryptic and the antibody cannot bind to the La protein.

Further preferred anti-La antibodies are 312B, 27E, 2F9, 32A or antibodies with the CDRs of the variable regions of the light chains ($V_L$) and/or heavy chains ($V_H$) selected from the SEQ ID Nos. 27 to 50 (preferably in the combinations set forth in the Tables 5 to 8). These bind to split, conformation-dependent epitopes in the human La protein which comprise the areas of the amino acid sequences of amino acid 10-20 and amino acid 94-100 (in the above inserted Table and in the following also "10-100") of the human La protein. The inventors have found that these epitopes are sensitive to oxidation.

These anti-La antibodies recognize exclusively the reduced form (i.e. native form) of the La protein and not the oxidized form. Because in some tumors hypoxic conditions are present, these anti-La antibodies are particularly suitable for such hypoxic tumors, in particular when an anti-La targeting is desired without combination with therapies (in particular chemotherapy and/or radiation therapy) which cause oxygen stress and thus an oxidation of the La protein. Hypoxic conditions are to be understood as oxygen depletion (i.e. an oxygen concentration which is (significantly) lower than that in healthy tissue). This oxygen depletion often originates in solid tumors, in particular when the tumor (or parts thereof) is growing faster than the blood-supplying tissue. This is a special advantage because hypoxic tumors are often resistant against chemotherapy and radiation therapy.

Anti-La antibodies that are also preferred are 22A and 24BG7 or antibodies with the CDRs of the variable regions of the light chains ($V_L$) and/or heavy chains ($V_H$) selected from the SEQ ID Nos. 15 to 26 (preferably in the combinations set forth in Tables 3 and 4). These bind to split epitopes in the human La protein which comprise the regions of the amino acid sequences of amino acid 107-116 and amino acid 185-200 (in the following also "107-200") of the human La protein.

The antibodies according to the invention were obtained by different immunization methods (see FIG. 2). In healthy individuals no immunological reactions take place against the body's own proteins because auto-reactive T cells and B cells are eliminated during their development. This tolerance and the homology between hLa and mLa may be the reason that mice hardly developed antibodies against rhLa protein after conventional immunization with recombinant human La protein (rhLa). After a plurality of fusions (greater than 50) only the two mAks 5B9 and 7B6 were obtained. Instead, a strong B cell response against the hLa antigen in hLa transgenic mice was induced by adoptive T cell transfer and several mAks could be obtained therefore from one mouse.

The isotypes of the antibodies according to the invention and the immunization methods for their production are summarized in the following Table 12:

TABLE 12

| Antibody | Isotype | Preparation |
|---|---|---|
| 7B6 | IgG1 | immunization with rhLa protein |
| 5B9 | IgG2a | immunization with rhLa$_{1-192}$ |
| 24BG7 | IgG1 | immunization of mice transgenic for human La protein (hLaTg), adoptive T cell transfer |
| 22A | IgG1 | hLaTg, adoptive T cell transfer |
| 27E | IgG2b | hLaTg, adoptive T cell transfer |
| 312B | IgG1 | hLaTg, adoptive T cell transfer |
| 2F9 | IgG1 | hLaTg, adoptive T cell transfer |
| 32A | IgG1 | hLaTg, adoptive T cell transfer |

All antibodies according to the invention are capable of recognizing recombinant human La protein (rhLa, independent of whether prokaryote-produced or eukaryote-produced) and native human La protein in immunoblot (western blot). The antibodies 22A and 32A are advantageously specific for the human La protein and cannot bind the related murine La protein at all. mAk 7B6 differentiates between prokaryote-produced and eukaryote-produced murine La proteins (mLa) and recognizes only the bacterial, probably not post-translationally modified, variant of the murine La protein (see FIG. 4). The mAks 22A, 27E and 312B show the strongest binding to human La protein in immunoprecipitations. 312B was suited best for the precipitation of the mLa protein (FIG. 5).

In the following Table 13, the reactivities of the antibodies according to the invention in immunoblot, in immunoprecipitation and immune fluorescence are summarized:

TABLE 13

| | Reactivity in immunoblot against | | | Reactivity against 3T3 transgenic | | Immuno-precipitation | | Immunofluorescence after para-formaldehyde (PFA) fixation | | |
|---|---|---|---|---|---|---|---|---|---|---|
| | | | human cells | murine cells | for hLa in immunoblot | | from 3T3 LaG total extract | | human cells | murine cells |
| mAk | rhLa | rmLa | (HeLa) | (3T3) | hLa | mLa | hLa | mLa | (HeLa) | (3T3) |
| 7B6 | +++ | ++ | +++ | − | ++ | − | − | − | (+) | − |
| 5B9 | +++ | +++ | +++ | +++ | +++ | +++ | − | − | ++ | − |
| 24BG7 | +++ | + | +++ | + | ++ | + | + | − | ++ | ++ |
| 22A | +++ | − | +++ | − | + | − | ++ | − | ++ | − |
| 27E | +++ | + | +++ | +++ | ++ | ++ | + | + | +++ | +++ |
| 312B | +++ | +++ | +++ | +++ | + | ++ | +++ | +++ | +++ | +++ |
| 2F9 | +++ | +++ | ++ | ++ | + | + | − | − | + | + |
| 32A | +++ | − | ++ | − | (+) | − | − | − | (+) | − |

3T3 LaG: murine cells transgenic for hLa. The evaluation of the binding strengths was carried out according to the following scale: − negative, +++ strongly positive, ++ positive, + weakly positive, (+) very weakly positive.

The affinities of the native antibodies are within the magnitude of $10^{-10}$ mol/l. The affinities of the recombinant derivatives reach $10^{-7}$ to $10^{-9}$ mol/l. Due to the high affinity, the CDR sequences according to the invention are suitable in particular for the production of recombinant fragments (like scFv) and for immunotargeting.

The term "antibody" in the meaning according to the invention encompasses all antibodies, antibody fragments and derivatives thereof which are able to bind to the antigen, in this case the human La protein, and comprise the CDRs according to the invention completely or partially. They include the complete monoclonal antibodies and also the epitope-binding fragments of these antibodies. In this context, the epitope-binding fragments (here also referred to as antibody fragments or antibody derivatives) comprise all parts of the antibody which are able to bind to the antigen, in this case the human La protein. Examples of preferred antibody fragments according to the invention include, but are expressly not limited to, Fab, Fab', F(ab')$_2$, Fd, individual chain (single chain) variable fragments (scFv), single chain antibodies, disulfide-linked variable fragments (sdFv), and fragments that contain either a variable region of the light chain ($V_L$) or a variable region of the heavy chain ($V_H$). Furthermore, included are recombinant antibodies, like diabodies, triabodies and tetrabodies.

Preferably, the antibody carries a marker molecule, as for example biotin, dioxygenin, a radionuclide or a fluorescent dye. It is particularly preferred that the antibody is conjugated with an effector group.

Antibody fragments contain the variable regions either alone or in combination with other regions which are selected from the hinge region, and the first, second and third segment of the constant region ($C_H1$, $C_H2$, $C_H3$). Also encompassed by the term "antibody" are chimeric antibodies where different parts of the antibody originate from different species, as for example antibodies with a murine variable region which is combined with a human constant region.

Antibody fragments are linked optionally with each other by a linker peptide. The linker peptide comprises a short (preferably having a length of 10 to 20 amino acid residues), flexible peptide sequence which is selected such that the antibody fragment has such a three-dimensional folding of the $V_L$ and $V_H$ that it exhibits the antigen specificity of the complete antibody. Preferred linker peptides are glycine-serine linkers with the structure $(Gly_xSer)_y$ with x and y selected from 1 to 10, preferably 3 to 5. Furthermore, linker peptides are preferred which are comprised of a peptide sequence which can increase the protease resistance of the antibody derivatives. Particularly preferred are linker peptides according to SEQ ID No. 85 (E7B6).

The term "variable region" is defined according to the invention as the parts of the heavy and light chains of the antibodies which differ between antibodies in their sequence and determine the specificity of the antibody and the binding action to its antigen. In this context, the variability is not distributed evenly in the variable region. It is usually concentrated within three defined segments of the variable region which are referred to as complementarity determining region (CDRs) or also hypervariable regions and exist in the variable regions of the light as well as the heavy chains. The more strongly preserved parts of the variable regions are called frame regions (framework regions). The variable regions of the heavy and light chains contain four framework regions which adopt predominantly a beta sheet structure, wherein every framework region is connected with three CDRs which form loops which connect the beta sheet structures and in some cases form a part of the beta sheet structure. The CDRs of the respective chain are brought into immediate proximity by the framework regions and contribute together with the CDRs of the other chain to the formation of the antigen binding region of the antibodies.

The constant region (Fc) of the antibodies is not involved in antigen binding but offers, instead, varied effector functions which are triggered by binding to the appropriate Fc binding receptors, as for example the induction of the antibody-dependent cellular cytotoxicity (ADCC).

Preferably, the antibodies according to the invention comprise at least one variable region of the heavy chain ($V_H$) and a variable region of the light chain ($V_L$) in form of an scFv. In this context, the variable region of the heavy chain ($V_H$) and the variable region of the light chain ($V_L$) each contain at least one of the CDR sequences according to the invention.

In the antibodies according to the invention certain amino acids of the specific amino acid sequences can be exchanged in such a way that they maintain the binding properties of the anti-La antibody, but differ in their sequence by exchange, deletion or addition of one or several amino acids. Encompassed are therefore also antibodies which contain structures whose amino acid sequences, compared to the amino acid sequences according to the invention of the variable regions selected from the sequences according to SEQ ID Nos. 51 to 66, have a sequence identity of preferably at least 70%, particularly preferred at least 80%, in particular at least 90%, or contain appropriate humanized sequences and that bind the antigen La, wherein these sequences comprise six of the CDRs according to SEQ ID Nos. 3 to 50 in combinations that are presented in the Tables 1 to 8.

In special embodiments of the invention, the antibody comprises in addition to the amino acid sequences according to the invention of the variable regions or appropriate humanized sequences, the following structures:
 a constant region of a heavy chain of a human IgG,
 a region $C_L$ of the human kappa light chain
 and a human IgG hinge region,
optionally in the form of a F(ab)$_2$-fragment.

In a particularly preferred embodiment of the invention, antibodies in the form of scFv fragments which comprise at least one variable region of the heavy chain ($V_H$) and/or a variable region of the light chain ($V_L$) which contain CDR regions according to the invention. Furthermore, particularly preferred are antibodies in the form of scFv fragments which comprises at least one of the variable regions according to the invention of the heavy and/or light chain.

The invention encompasses murine anti-La antibody and humanized versions of these antibodies.

The goal of the humanization of antibodies resides in the reduction of the immunogenitity of a xenogenic antibody, like in this case of the murine antibody, for the use in the human system, wherein the full binding affinity and the antigen specificity is preserved. Humanized antibodies can be produced in different ways, as for example by resurfacing and CDR grafting. In resurfacing, all non-CDR regions on the surface of the antibody are changed by a combination of molecular modeling, statistical analyses and mutagenesis so that they resemble the surface of antibodies of the target organism. In CDR grafting, the CDR regions according to the invention are introduced into human variable regions.

Humanized antibodies which contain the CDR regions according to the invention are expressly considered to be components of the invention.

Components of the invention are also antibodies which are conjugated with an effector group. Conjugation is to be understood here as coupling of a substance to an antibody. Coupling of the antibody with the effector group is produced preferably by expression as a fusion protein or by in vitro methods wherein the effector group is preferably coupled by linker groups to the antibody (for example, by thioether bonds or disulfide bonds). They can be bound also to the antibody by an intermediary carrier molecule, for example, serum albumin. Optionally, an antibody also contains several effector groups.

In this context, the effector groups are preferably pharmaceutically effective substances (active substances). Preferred active substances comprise, but are not limited to, toxins, like cytostatic agents, for example, maytansinoids and maytansinoid analogues, taxoids, CC-1065 and CC-1065 analogues, dolastatin and dolastatin analogues, methotrexat, daunorubicin, doxorubicin, vincristin, vinblastin, melphalan, mitomycin C, chlorambucil and calicheamicin. The invention also encompasses antibodies which are conjugated with radionuclides as effector groups and their use for the therapy and diagnostics, in particular of tumors. Suitable radionuclides are preferably the radioactive isotopes of technetium, rhenium, yttrium, copper, gallium, indium, bismuth and platinum, as for example $^{99m}$Tc, $^{90}$Y, $^{186}$Re, $^{188}$Re, $^{68}$Ga and $^{111}$In.

Effector groups according to the invention comprise furthermore enzymes (particularly enzymes that are suitable for the ADEPT system), co-stimulatory molecules (e.g., CpG) or also nucleic acids. The antibody that is conjugated with an effector group can be present optionally in the form of a fusion protein.

Subject matter of the invention are also recombinant antibodies, containing:
 i. a binding unit of an antibody that binds specifically to an epitope of a human nuclear antigen, preferably human La protein, as well as
 ii. a binding unit
  of an antibody which binds specifically to an effector cell or
  of a ligand which binds specifically to an effector cell.

The antibody or ligand which binds specifically to an effector cell is selected preferably from antibodies and ligands which bind specifically surface structures on T lymphocytes, NK cells, dendritic cells, granulocytes and/or monocytes.

The epitope, which the antibody which binds specifically to an epitope of a human nuclear antigen, is accessible preferably only under oxidizing conditions. Such a preferred antigen which is recognized by anti-La 7B6 is indicated in SEQ ID No. 84.

Components of the invention are therefore also recombinant antibodies which are conjugated with a further antibody, antibody fragment or ligand which is directed against an antigen that is different from the human nuclear antigen, in particular the human La protein. The recombinant antibody is preferably a bispecific antibody. The bispecific antibody is preferably a single chain bispecific diabody (scBsDb). In this case, two scFv fragments are connected to each other by a short linker (preferably of a length of 10 to 20 amino acid residues). Particularly preferred, the bispecific antibody is a single chain bispecific tandem antibody (scBsTaFv). In this case the two scFv fragments are connected by longer linker peptides (preferably of a length of from 18 to 50 amino acid residues) which results in an especially flexible structure.

Preferably, the recombinant antibodies according to the invention contain, in addition to the La antibody according to the invention, an antibody, antibody fragment or ligand which is directed specifically against surface antigens of effector cells, as for example T cells, particularly cytotoxic T cells, NK cells, monocytes, macrophages, dendritic cells, or granulocytes. The definition of effector cells in accordance with the invention encompasses all the cells of the innate and adaptive immune system which provide immunological reactions or are involved actively therein. These antibodies are particularly preferably directed against the following surface structures on effector cells: CD3, CD8, CD4, CD25, CD28, CD16, NKG2D, NKp46, NKp44, activating KIR receptors (activating killer cell immunoglobulin-like receptors).

Also components of the invention are recombinant antibodies which comprise in addition to the La antibody according to the invention a ligand which influences the activity of effector cells by binding to the surface of the effector cells. The ligand is selected in this context such that it binds specifically to surface structures of effector cells and triggers upon binding signal cascades for the activation of the effector cells. Preferred as a ligand is a protein structure or a glycan which binds specifically to a receptor which is expressed specifically on the surface of effector cells, wherein the ligand causes an activation of the effector cell by its binding to the receptor. Particularly preferred, the protein structures are selected from ULB-Ps (e.g., ULB-P2), MICA, MICB, as well as cytokines (as for example IL2 and IL15) and their fusion proteins.

Binding of the anti-La antibody according to the invention to the further antibody, antibody fragment or to the protein structure is produced preferably by an expression as a fusion protein or by in vitro methods, wherein the further antibodies, antibodies or protein structures are bound preferably by linkers, like peptide linkers, to the antibody.

The invention comprises furthermore nucleic acid sequences which encode for an antibody according to the invention, as well as vectors which contain the nucleic acid sequences.

The vector (expression vector) is in each case preferably a plasmid, an artificial chromosome or even a virus particle or another vector which contains an expression cassette which is incorporated stably in the genome of the host (host cell or host organism).

Preferably, the nucleic acid sequences which code for an antibody according to the invention contain the sequences which code for the CDRs mentioned above (selected from SEQ ID Nos. 3 to 50 in the combinations set forth in Tables 1 to 8) of the variable regions of the heavy chains ($V_H$) and the light chains ($V_L$).

In another preferred embodiment of the invention, the nucleic acid sequences contain sequences which code for the variable regions of the heavy chains ($V_H$) and/or the light chains ($V_L$) selected from SEQ ID Nos. 51 to 66.

Components of the invention are also host cells or non-human host organisms which contain a nucleic acid sequence according to the invention.

A host cell is a naturally occurring cell or a transformed or genetically modified cell line or a (multicellular) non-human host organism which contains the expression system according to the invention (i.e. at least one expression vector). In this context, the invention comprises transient transfectants (e.g., by mRNA injection), i.e., hosts (host cells or host organisms) in which the expression system is contained as a plasmid or artificial chromosome, as well as hosts in which the expression system is integrated stably into the genome of the host (or single cells of the host). The host cell is selected preferably from prokaryotes or eukaryotes. Preferred prokaryotes are selected from *Escherichia coli* and *Bacillus subtilis*. Preferred eukaryotes are yeast cells (e.g., *Saccharomyces cerevisiae, Pichia pastoris*), insect cells, amphibian cells or mammalian cells, as for example CHO, HeLa, Hek293T, Hek293A. Preferred host organisms are plants, as for example maize or tobacco, invertebrates or vertebrates, in particular *Bovidae, Drosophila melanogaster, Caenorhabditis elegans, Xenopus laevis, Medaka*, zebra fish or *Mus musculus*, or cells or embryos of the aforementioned organisms.

The invention encompasses furthermore a pharmaceutical composition which contains one or several antibodies according to the invention in association with a pharmaceutical suitable diluent or carrier. Preferably, the pharmaceutical composition is present in a form suitable for intravenous administration.

Preferably, the composition comprises a chimeric or humanized antibody with a reduced immunogenicity which contains the CDR regions according to the invention.

The pharmaceutical compositions according to the invention comprise different dosage forms. The pharmaceutical compositions are administered preferably parenterally, particularly preferred intravenously. In one embodiment of the invention, the parenteral pharmaceutical composition is present in an administration form which is suitable for injection. Particularly preferred compositions are therefore solutions, emulsions or suspensions of the antibody which is present in a pharmaceutical suitable diluent or carrier.

As carriers, preferably water, buffered water, 0.4% saline solution, 0.3% glycine and similar solvents are used. The solutions are sterile. The pharmaceutical compositions are sterilized by customary, well known technologies. The compositions contain preferably pharmaceutical acceptable excipients, as for example those that are required to provide approximately physiological conditions and/or to increase the stability of the antibody, as for example agents to adjust the pH value and buffering agents, agents for adjusting the toxicity and the like, preferably selected from sodium acetate, sodium chloride, potassium chloride, calcium chloride and sodium lactate. The concentrations of the antibodies according to the invention in these formulations are variable depending on the application; they amount preferably to less than 0.01% by weight, preferably at least 0.1% by weight, further preferred between 1 and 5% by weight, and they are selected primarily on the basis of fluid volume, viscosity, and the like or in accordance with the respective mode of administration.

The antibodies according to the invention are preferably taken up in a composition which is suitable for parenteral administration. Preferably, the pharmaceutical composition is an injectable buffered solution which contains between 0.1 to 500 mg/ml of antibody, particularly preferred between 0.1 to 250 mg/ml of antibody, in particular together with 1 to 500 mmol/l (mM) of a buffer. The injectable solution can be present in a liquid as well as a lyophilized dosage form. The buffer can be preferably histidine (preferably 1 to 50 mM, particularly preferred 5 to 10 mM) at a pH value of from 5.0 to 7.0 (particularly preferred at a pH value of 6.0).

Other suitable buffers comprise, but are expressly not limited to, sodium succinate, sodium citrate, sodium phosphate or potassium phosphate. Sodium chloride is preferably used between 0 to 300 mM, particularly preferred 150 mM for a liquid administration form. For a lyophilized administration form the pharmaceutical composition contains preferably an antifreeze agent, preferably 0-10% sucrose (particularly preferred 0.5-1.0%). Other antifreeze agents encompass trehalose and lactose. For a lyophilized administration form the pharmaceutical composition contains preferably expanding agents, preferably 1 to 10% mannitol. Other expanding agents comprise glycine and arginine. In liquid as well as in lyophilized administration forms stabilizers are preferably used, particularly preferred between 1 to 50 mM of L-methionine (particularly preferably between 5 and 10 mM).

In a preferred embodiment, the pharmaceutical composition comprises the antibody in a dosage amount from 0.1 mg/kg to 10 mg/kg per administration. Particularly preferred dosage amounts comprise 1 mg/kg of body weight.

Pharmaceutical compositions must be sterile and stable under the production and storage conditions. The composition can be formulated as a solution, microemulsion, dispersion, in liposomes or another ordered structure which is suitable for high concentrations of antibody. Sterile injectable solutions can be produced in that the necessary amount of the antibody is taken up in a suitable solvent, with one or with a combination of the above enumerated ingredients as needed, followed by filtration sterilization. For sterile, lyophilized powders for preparing sterile injectable solutions the preferred preparation procedures are vacuum drying and spray drying which results in a powder of the antibody plus any additional desired ingredients from a solution thereof that has been sterile-filtered beforehand.

The invention encompasses the use of the antibody according to the invention as a medicament.

The invention also encompasses a method for treating a human being having a tumor disease by administering an antibody according to the invention.

Tumor diseases mean in particular acute myeloid leukemia (AML), chronic myeloid leukemia (CML) and pro-myeloid leukemia (PML) and other illnesses such as myelodysplastic syndrome (MDS). In addition to hematologic tumors, the anti-La antibodies according to the invention are suited in particular for the therapy of solid tumors, e.g., of the prostate, pancreas, colon, lung, mamma cancer, cancer of the thyroid, melanoma, brain tumors (e.g., glioblastomas) as well as head and neck lymphomas.

Advantageously, the invention is suited in particular for immunotherapy of so-called "immune escape" variants of tumors, i.e. tumors which have stopped or down-regulated the expression of tumor antigens in order to escape the immune system. According to the invention, no antibody is used for tumor targeting which is directed against a tumor antigen but against a nuclear antigen. By the recombinant antibodies according to the invention which bind the La protein (or another nuclear antigen) on the surface of tumor cells as well as effector cells and thus recruit them to the tumor cells, tumor cells can thus be targeted with an antigen on the surface which is expressed in all cells as a nuclear antigen constitutively and is not tumor-specific.

Particularly preferred for an immunotherapy is the antibody 7B6 or an antibody with the aforementioned CDRs of the variable regions of the light chains ($V_L$) and heavy chains ($V_H$) (SEQ ID Nos. 9 to 14) and preferably the variable regions of the light chains ($V_L$) and/or heavy chains ($V_H$) according to SEQ ID Nos. 53 and 54 or corresponding humanized structures. As already discussed above, this antibody binds a redox-dependent epitope, which is released under the conditions of "oxidative stress" as it is particularly existing in tumor tissue. The fact that the 7B6 epitope under these oxidative conditions becomes accessible in La enables a more specific anti-tumor therapy with reduced side effects.

For therapeutic uses a sterile pharmaceutical composition, containing a pharmacologically effective dosage amount of one or several antibodies according to the invention, is administered to a patient in order to treat the aforementioned illnesses.

Killing of the tumor cells is achieved preferably by the recruitment of effector cells. As an alternative, or in addition, by the specific transport of pharmacological active substances (e.g., toxins) and the release thereat.

In a special embodiment of the invention, an antibody is used in the form of a bispecific antibody. In this context, the bispecific antibody in a particularly preferred embodiment of the invention contains at least a binding unit of an antibody that specifically binds to an epitope of a human nuclear antigen, preferably human La, as well as a binding unit which is directed against a surface structure on NK cells, preferably against ULB-P2 (i.e. preferably a binding unit of an anti-ULB-P2 or of the ULB-P2 ligand). Preferably, the bispecific antibody is used for the treatment of AML, as well as prostate cancer.

In a further especially preferred embodiment of the invention, the bispecific antibody contains at least a binding unit of an antibody that binds specifically to an epitope of a human nuclear antigen, preferably human La, as well as a binding unit which is directed against a surface structure on T cells, preferably against CD3 or CD8. Preferably, the bispecific antibody is used for the treatment by AML as well as prostate cancer.

In both aforementioned preferred embodiments of the invention the binding unit of the antibody which binds specifically human La contains preferably 6 CDRs according to SEQ ID Nos. 3 to 50 in a combination presented in the Tables 1 to 8.

In addition to the application in medicine for therapeutic purposes, the antibodies according to the invention are suited for diagnostics, biological research and other applications in which the detection of the La protein is of interest. Such uses are in particular western blot, immune staining of cells (e.g., for flow cytometry and microscopy) and ELISA, as well as the use as a tracer in imaging technologies as for example CT (computer tomography), PET/CT (positron emission tomography).

The invention also encompasses a method for producing an antibody with the steps:
  a. immunization of a first recipient with antigen wherein the antigen is a foreign antigen for the first recipient,
  b. isolation of T lymphocytes from the immunized recipient,
  c. transfer of the isolated T lymphocytes into a second recipient which expresses the antigen, i.e. the antigen is an auto-antigen for the second recipient,
  d. isolation of antibody-producing B cells from the second recipient.

Step a. corresponds to a classical immunization. The immunization can be carried out with or without adjuvant, e.g., with peptides or recombinant protein.

The first and second recipients are selected preferably from non-human vertebrates or non-human mammals, in particular rodents, like mice, hamsters or rats.

The antigen is for the first recipient a foreign antigen, i.e. the first recipient does not express the antigen.

Between steps b. and c. an enrichment of CD4 cells is preferably carried out.

The second recipient in step c. expresses the antigen, preferably constitutively, particularly preferred as a transgene. This means for the second recipient that the antigen is an auto-antigen. With the exception of the expressed antigen the second recipient is otherwise genetically identical to the first recipient as much as possible.

After step d. a selection of antigen-specific B cells, hybridoma generation and screening of generated hybridomas, and antibody production according to conventional methods, or the production and screening of recombinant antibody libraries, is carried out.

Preferably, the variable regions of the light chain ($V_L$) and the variable region of the heavy chain ($V_H$) of the antigen-recognizing B cells are sequenced and the CDRs are determined. Based on these sequence data, recombinant antibody fragments and/or humanized antibodies can be produced advantageously.

BRIEF DESCRIPTION OF THE DRAWINGS

The following figures and embodiments explained the invention in more detail without limiting the invention to them. The data of the monoclonal antibody SW5 are given as a comparative example.

FIG. 2A) The mAks 7B6 and 5B9 were obtained from wild type (wt) mice which had been immunized either with recombinant human La protein (rhLa) or with rhLa1-192 antigens. FIG. 2B) The remaining mAks come from one single mouse. The latter was transgenic for hLa (hLaTg) and received T cells from a wt mouse which had been immunized before with rhLa.

Total extracts were produced from the different hybridoma cells and applied onto a 12% SDS gel. After electrophoresis and western blot on a PVDF membrane, hLa and mLa proteins were detected by anti-La-5B9 and anti-mouse-IgG-AP (AP=alkaline phosphatase). The secondary antibody (sek.) alone showed no protein band.

Figure 1A:
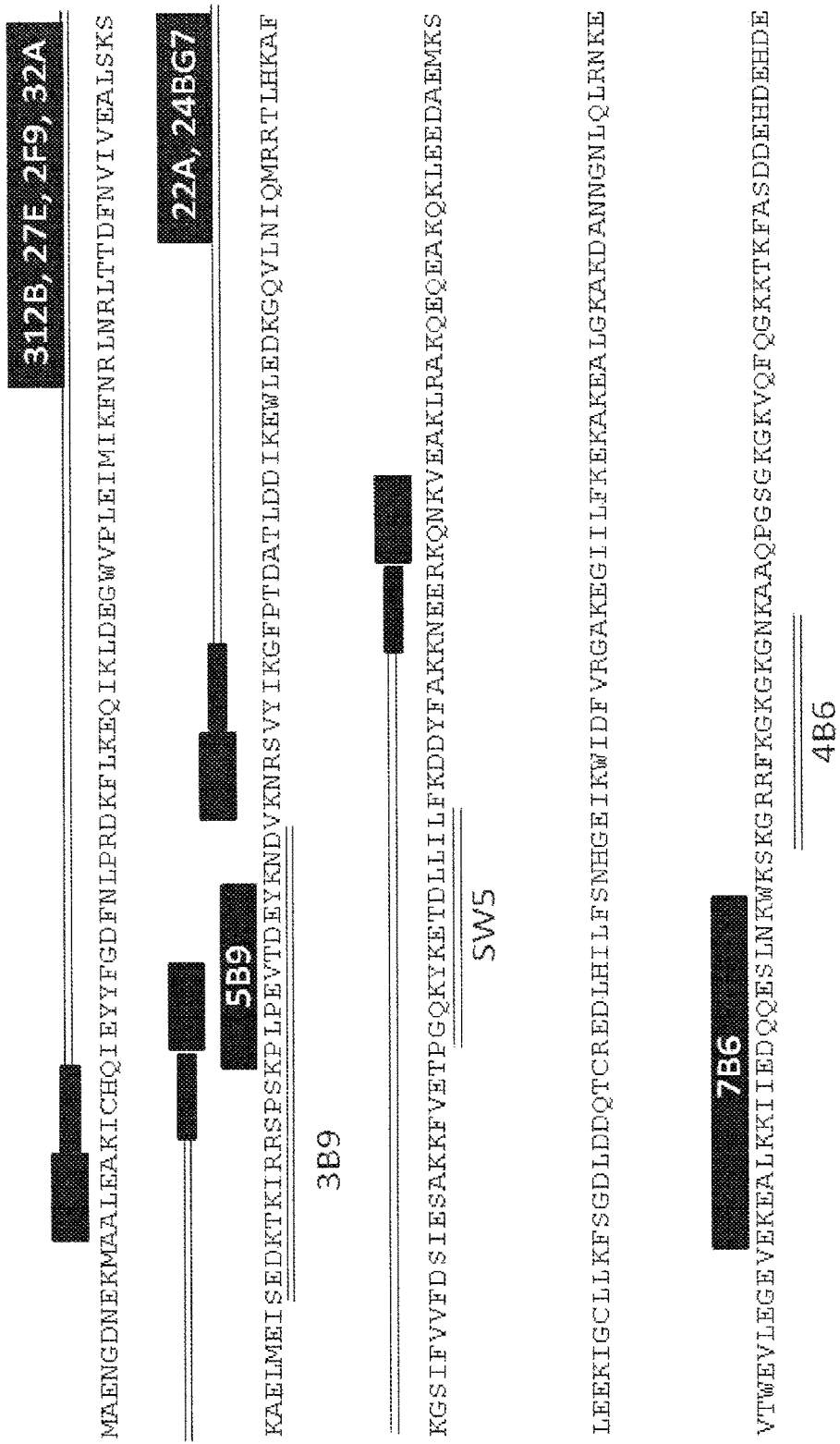
FIG. 1A shows the amino acid sequence of the human La protein (SEQ ID No. 1). In the sequence the epitopes which are recognized by antibodies (SW5, 3B9 as well as 4B6) known in the prior art are underlined twice. The epitopes that are recognized by the antibodies 5B9 and 7B6 according to the invention are marked by black bars. The two spatial epitopes (ACE 10-100 or 107-200) and the matching anti-La mAk (312B, 27E, 2F9, 32A, or 22A, 24BG7) are also indicated. It should be emphasized that a deletion/mutation of the first or last five amino acids (black wider bar) causes loss of reactivity.
Figure 1B:
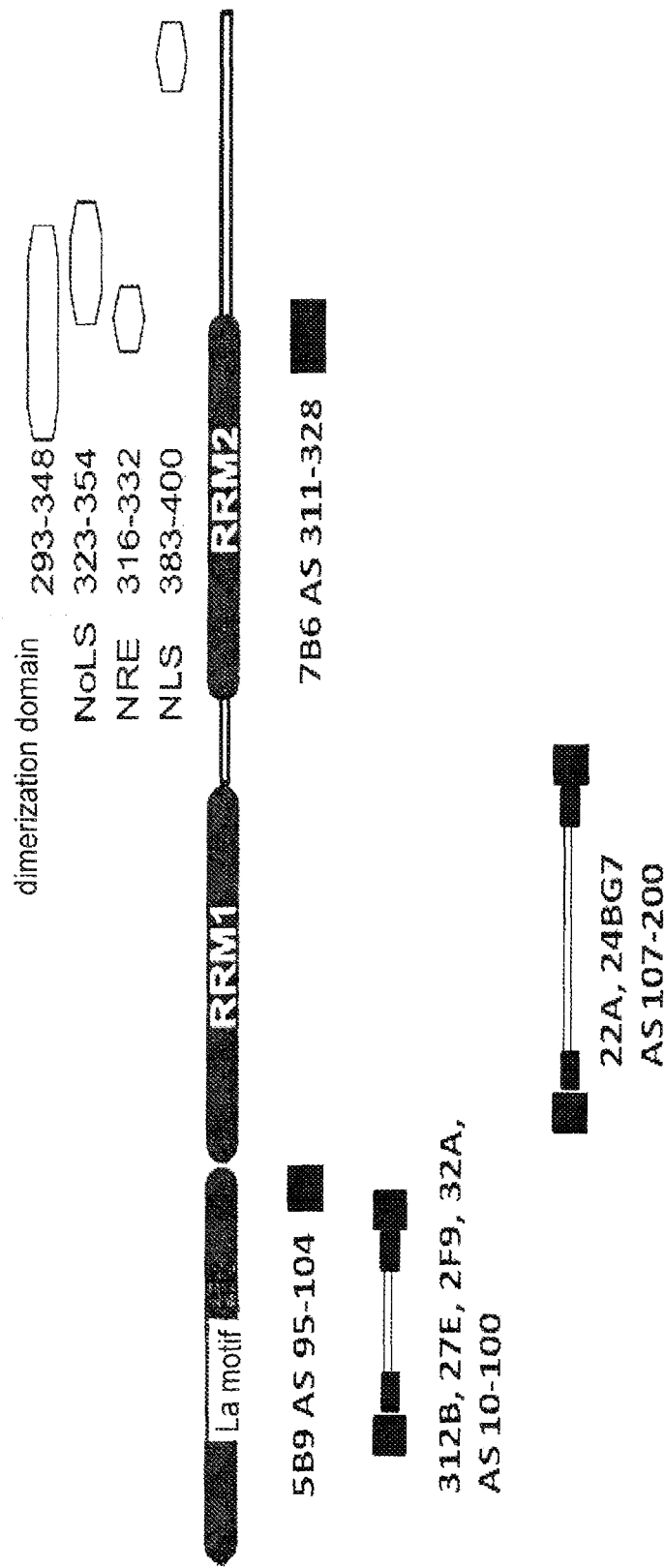
FIG. 1B shows a schematic illustration of the hLa protein with its three domains and functional areas. The different epitope regions are shown and the names of the mAks which bind them are indicated.
Figure 2A:
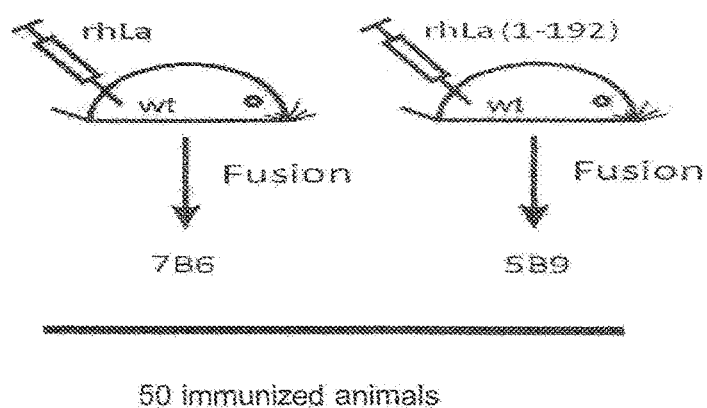
FIGS. 2A-2B explain the different technologies for the generation of the different anti-La-mAks.
Figure 2B:
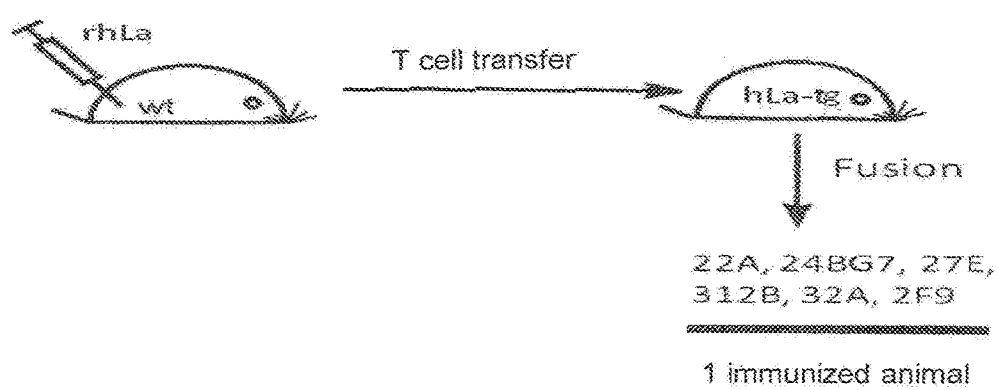
Figure 3:
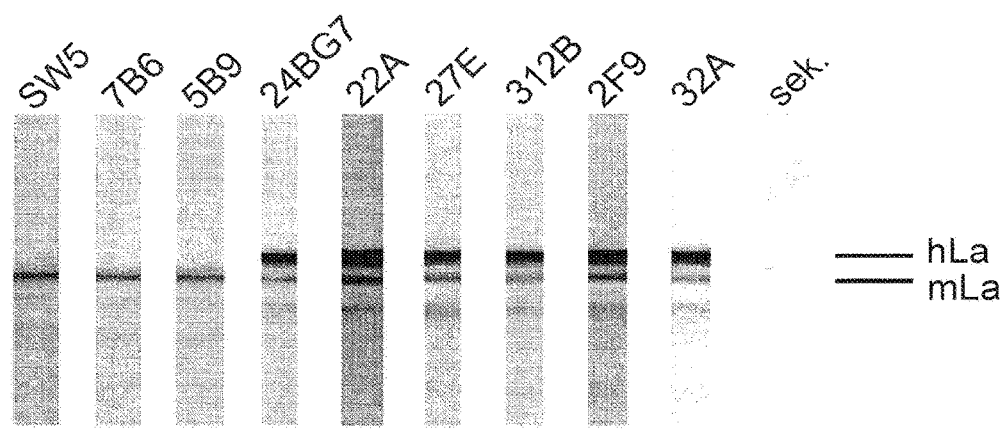
FIG. 3 shows the detection of the hLa-transgene in some of the hybridoma cells.
Figure 4:
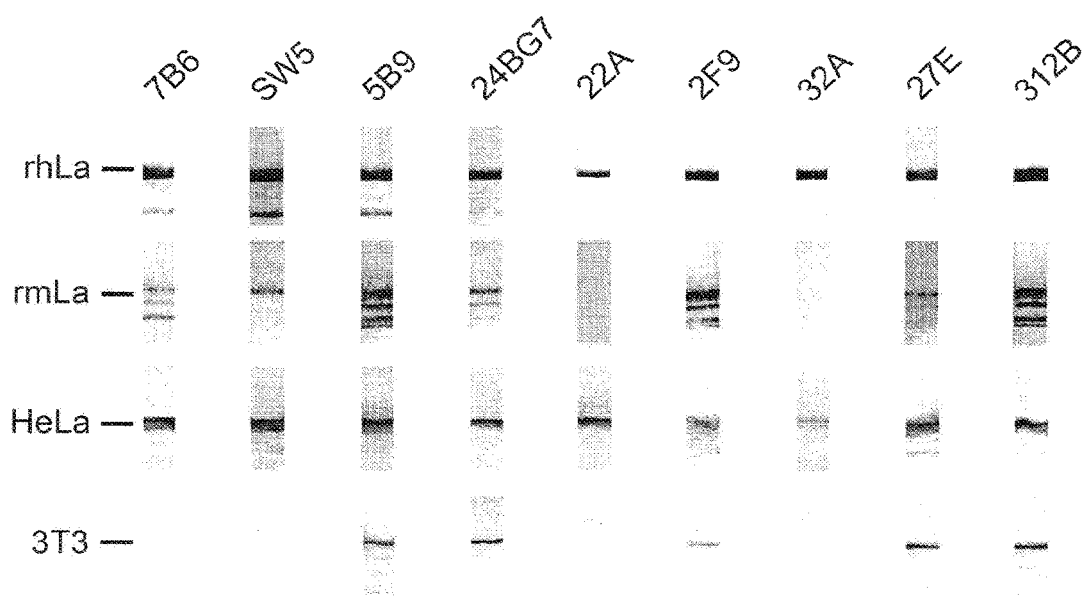

FIG. 4 shows the reactivity of the different mAks according to the invention against human and murine La protein by western blot (immunoblot). Bacterially produced recombinant human or murine La protein (rhLa or rmLa) as well as total extracts by human HeLa cells (DSMZ ACC 57) or by murine 3T3 cells (ATCC CRL 1658) were applied to four separate 12% polyacrylamide gels. After western blot each membrane was cut into strips which were incubated with the different hybridoma supernatents. The detection was done with anti-mouse-IgG-AP.

All antibodies recognized rhLa and eukaryotic hLa protein. The mAks 22A and 32A showed no reactivity at all towards rmLa and mLa, while 5B9, 24BG7, 2F9, 27E and 312B could recognize hLa as well as mLa. 7B6 and SW5 exhibited the special effect that they could stain bacterially produced rmLa but not eukaryotic mLa in immunoblot. The reason could be a post-translational modification of the protein in the respective epitope regions which is present in 3T3 cells but not in bacteria.

Figure 5:
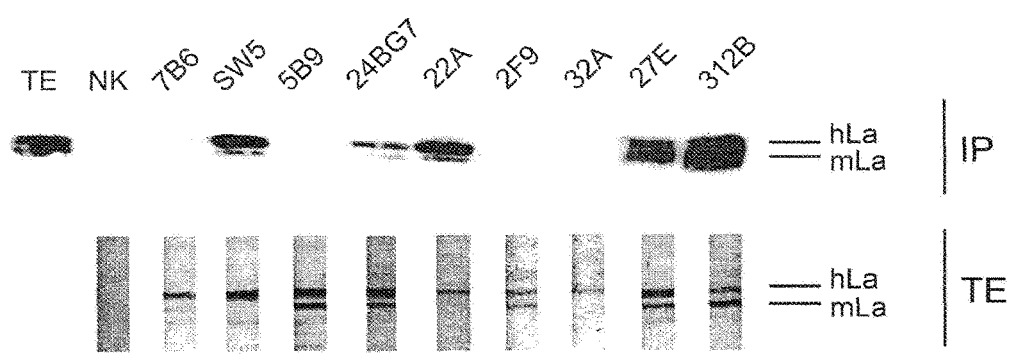

FIG. 5 shows immunoprecipitation (IP) of hLa and mLa with the different anti-La-mAks.

After precipitation of the immunocomplexes by True-Blot™ anti-mouse Ig IP beads and addition of SDS sample buffer, the samples were applied to a 12% polyacrylamide gel. SDS PAGE was followed by an electrophoretic transfer of the proteins onto a nitrocellulose membrane. After blocking of the membrane, the La proteins were detected with 5B9 hybridoma supernatent and mouse IgG TrueBlot™-POD. 3T3 LaG total extract (TE) served as a positive control. The different running behavior of hLa and mLa is recognizable as a double band. As a negative control (NK), no anti-La-mAk was added to evaluate the background resulting from the beads. Parallel to this, the reactivity was checked for every mAk individually against 3T3 LaG total extract by immunoblot. The detection was done with anti-mouse-IgG-AP.

The recognition and stable binding of the native antigen can be verified by immunoprecipitation. The La-anti-La immunocomplexes can be isolated by TrueBlot™ anti-mouse Ig IP beads and afterwards the La antigen can be detected by immunoblot. As a test system a total extract of a mouse-cell line which was stably transfected with hLa (3T3 Lying) was used. In this way, it was possible to test binding to both proteins at the same time. In addition, the total extract of these cells was applied to another SDS gel to check in parallel the reactivity of the hybridoma supernatents against both proteins by immunoblot.

Figure 6:
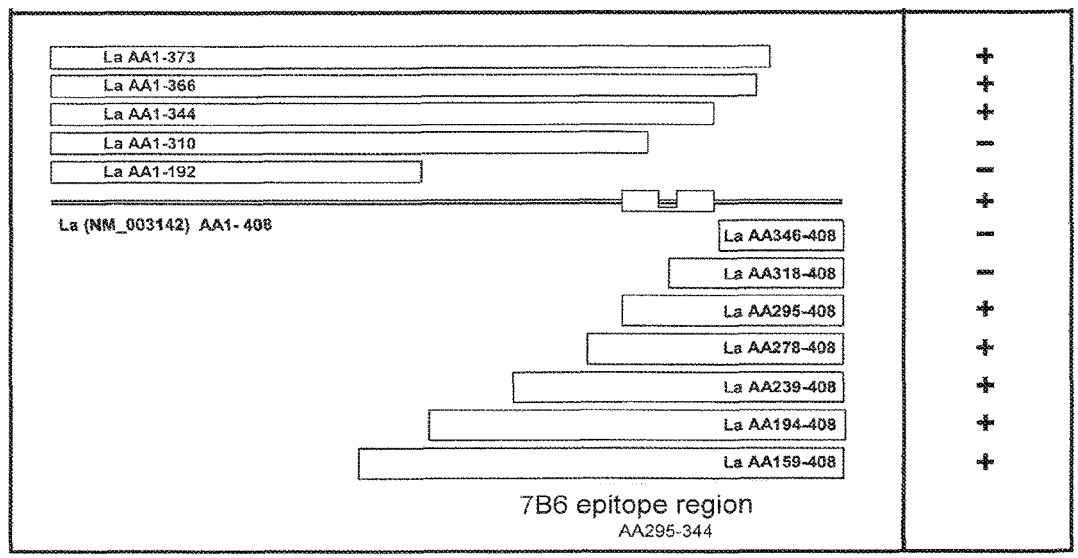
Figure 8:
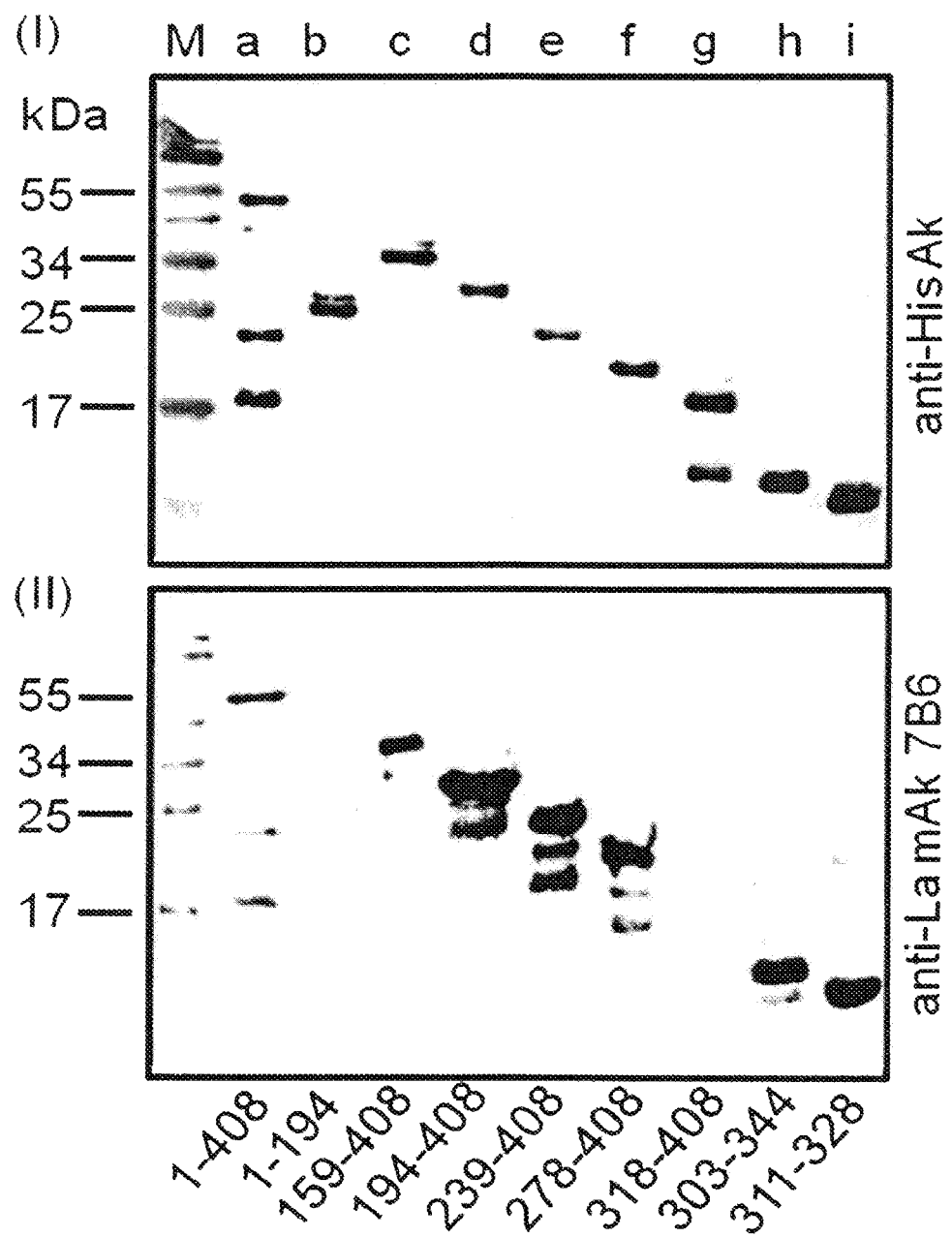

FIGS. 6 to 8 show the characterization of the peptide epitope recognized by the anti-La antibody 7B6.

For this purpose, a series of deletion mutants of the La protein was produced (FIG. 6 and FIG. 7). The purified proteins were analyzed by western blot (FIG. 8) with anti-penta HIS antibody (C (I)) and the anti-La mAk 7B6 (C (II)). In the left column of the FIGS. 6 and 7 the mutants are shown, respectively. The right column shows the reactivity in western blot. The results show that the antibody 7B6 recognizes the epitope with AA311 to 328 (SEQ ID No. 84).

FIGS. 9A-9C explain schematically the mechanism of action of the tumor therapy with the anti La antibodies according to the invention.

FIG. 9A: Cellular stress, e.g., by medicament (cytostatic agents, radio pharmaceuticals), radiotherapy or TAA-specific immuno-targeting, on a target cell from (target cell 1) leads to the induction of the cell death of the treated cell (target cell 1).

FIG. 9B: During the cell death the dying cell (target cell 1, 1) releases nuclear antigens (such as the La protein) from the nucleus which bind stably to the surface of the neighboring cell(s) (target cell 2).

FIG. 9C: Immune effector cells (here a T cell) are recruited by a bispecific antibody derivative (anti-La/anti-CD3) to the La-marked target cell 2. The bispecific antibody derivative is, on the one hand, directed against a peptide epitope in the La protein and binds, on the other hand, to an activating domain on the immune effector cell (here CD3 on T cells). By binding of La protein to neighboring cells and the recruitment of effector cells to the target cells, it is advantageously possible to destroy tumor cells (target cell 2) which had originally no specific target structure on the cell surface. Also, e.g. stroma cells or endothelial cells which supply the tumor cell can be destroyed in this manner.

Figures 10A, 10B, 10C, 10D, 10E, 10F, 10G, 10H:
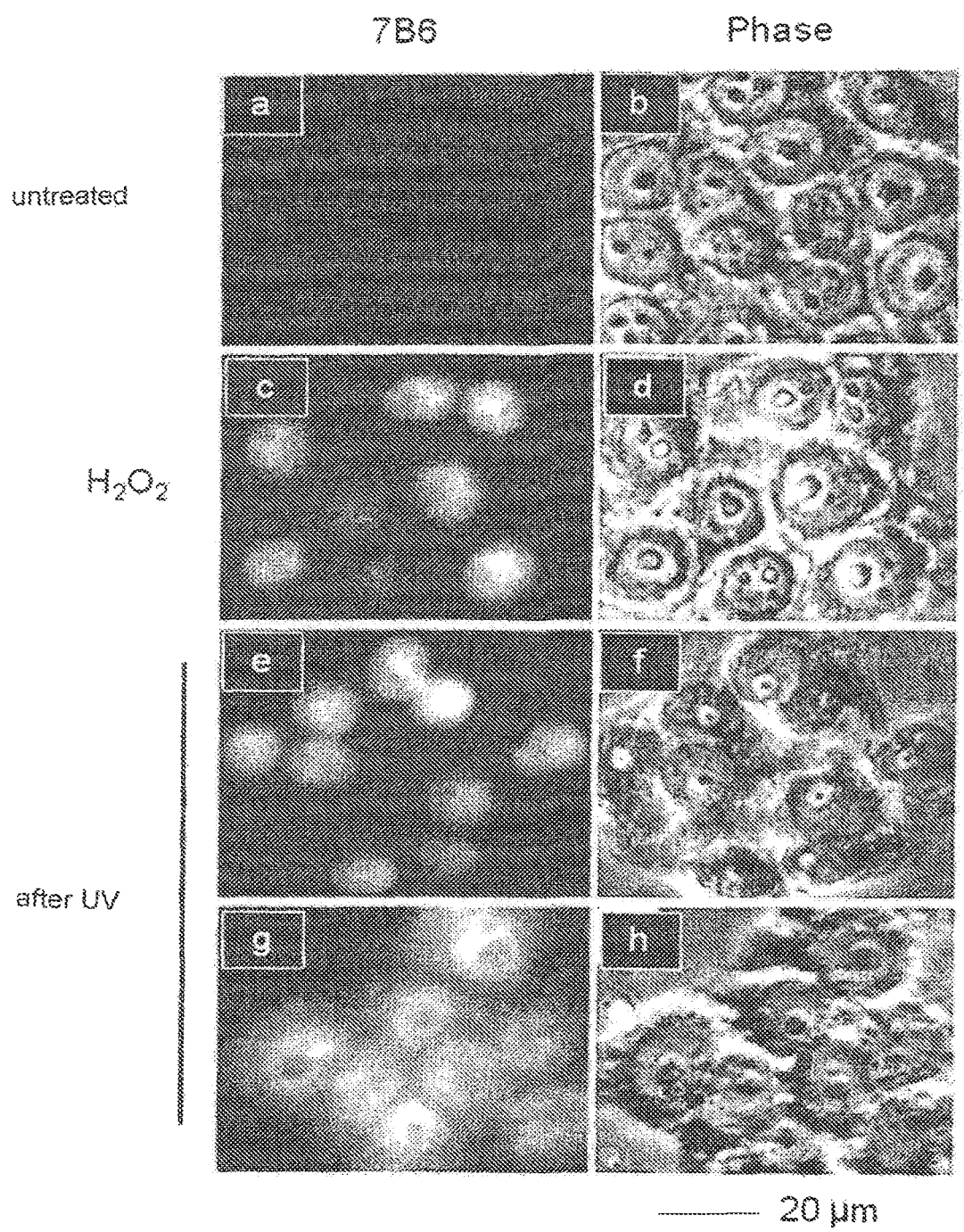

FIGS. 10A-10H show the redox sensitivity of the La antigen: The antibody 7B6 recognizes an oxidized variant. When human cell culture cells are fixed with methanol, the cells cannot be stained with the anti-La mAk 7B6 (FIG. 10A). When the cells are washed before staining with PBS containing $H_2O_2$ (FIG. 10C), then mAk 7B6 can however stain the cells. When oxidative stress is exerted on the cells before fixation (here by UV radiation), mAk 7B6 (FIG. 10E) is also able to stain the cells after fixation. When doing so, after UV exposure, dependent on time, a translocation into the cytoplasm (FIG. 10G) occurs. FIGS. 10B, 10D, 10F, and 10H are the corresponding phase contrast images to the epifluorescence images (FIGS. 10A, 10C, 10E, and 10G).

Figure 11A:
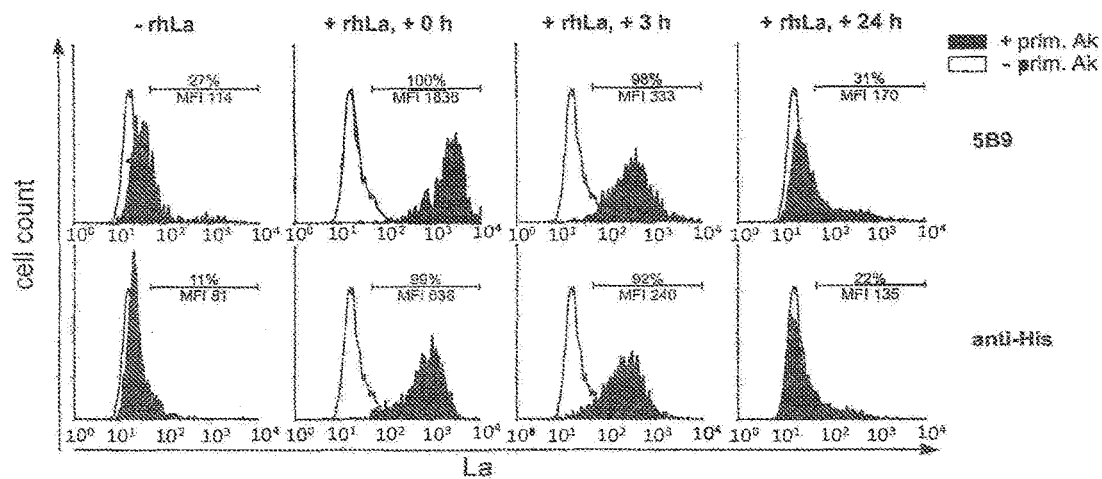
Figure 11B:
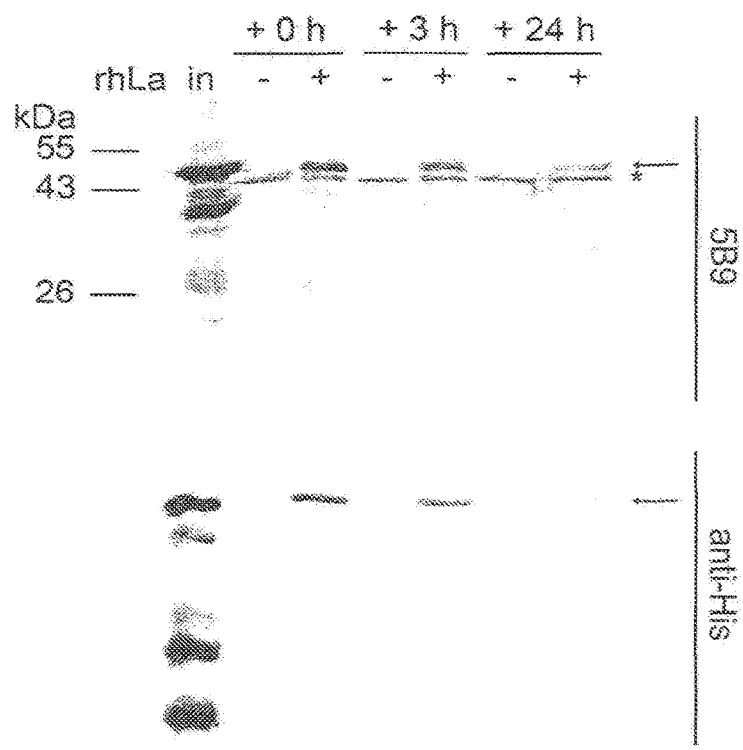

FIGS. 11A-11B show the stability of the rhLa protein on the cell surface of 3T3 cells up to 24 hrs.

The day before, mouse 3T3 cells were seeded into several 24-well plates. All cells were incubated in parallel for 1 hr. with 1.7 µM of rhLa protein in DMEM at 37° C. and then the material that was not bound is washed off. Untreated cells were carried along as a control.

FIG. 11A: The cells were stained either immediately (0 hrs.) on ice with 5B9 or anti-His (prime. Ak) and the anti-mouse-IgG-Alexa Fluor® 488-antibody, or they were transferred into medium and were cultured for another 3 hrs or 24 hrs in an incubator before they were also stained. After staining the cells were removed with PBS-EDTA and analyzed in a flow cytometer. The cells that had been cultured longer were accordingly stained and measured later. FIG. 11B: Western blot of the total extracts which had been produced immediately after La decoration, after 3 hrs. or 24 hrs. Parallel to this, samples with cells without La loading were carried along. In the first trace of the gel the amount of rhLa protein was applied which had been given also to the cells ("in"). The western blots were developed with 5B9 and anti-His as well as anti-mouse-IgG-AP. The arrow marks the band of the rhLa protein which could be detected with 5B9 and anti-His. (*) indicates the endogenous mLa protein which is also recognized by 5B9.

Figure 12A:
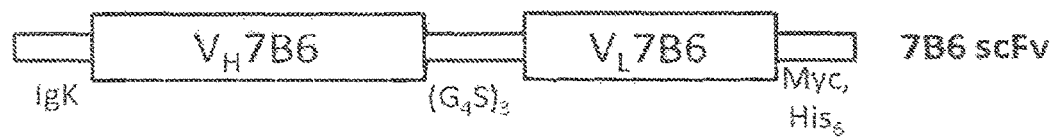
Figure 12B:
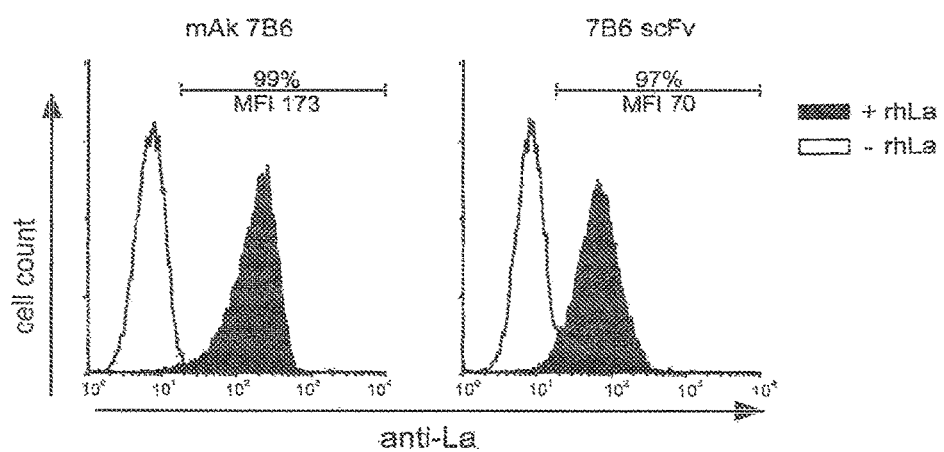

FIGS. 12A-12B show construction, eukaryote production as well as binding studies for the anti-La-scFvs.

FIG. 12A: In the anti-La-scFv molecule the variable domains of the mAks 7B6 are linked with each other in the order $V_H$-$V_L$ by a flexible glycine serine linker (($G_4S$)$_3$). The Igκ signal sequence coded by the vector pSecTag2 B enables the secretion of the proteins in the medium. A c-myc and a hexahistidine-($His_6$-) tag are added C-terminally. FIG. 12B: After purification of 7B6 scFv from the cell culture supernatent, binding of the protein (10 µg) on La-decorated tumor cells was examined. The detection was carried out with anti-c-myc-FITC. Parallel to this, cells were stained with mAk 7B6 and anti-mouse-IgG-Alexa Fluor® 488. Moreover, cells were incubated with the antibodies, respectively, without prior La loading (−rhLa).

FIGS. 13A-13E show construction, purification and binding studies of the bispecific antibody CD3x7B6.

Figure 13A:
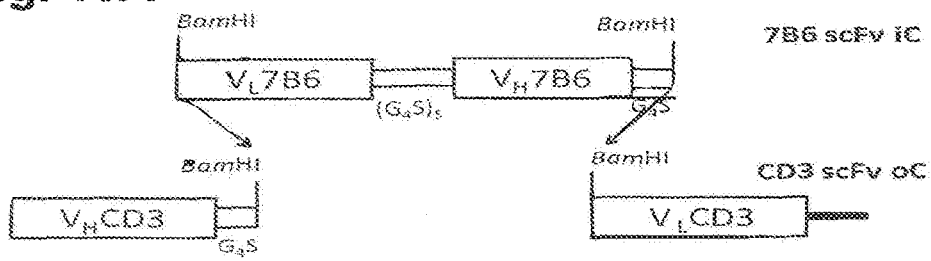
Figure 13B:
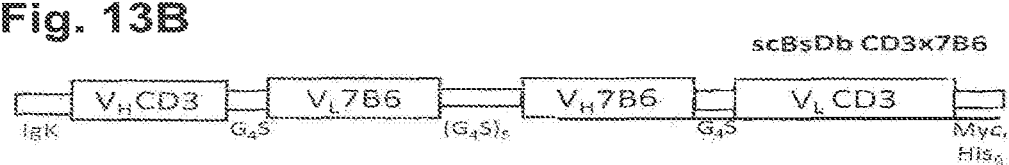
Figure 13C:
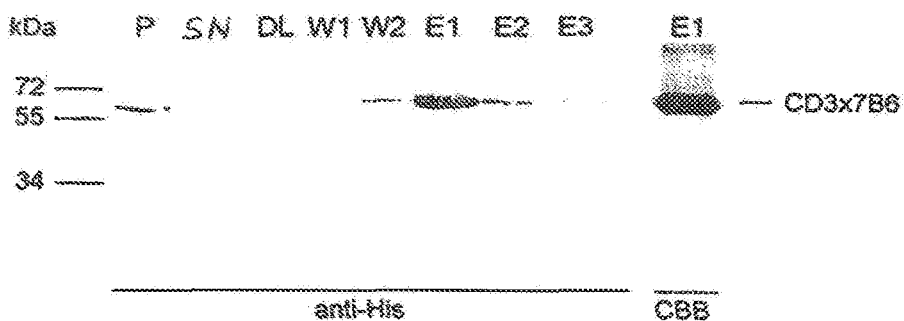
Figure 13D:
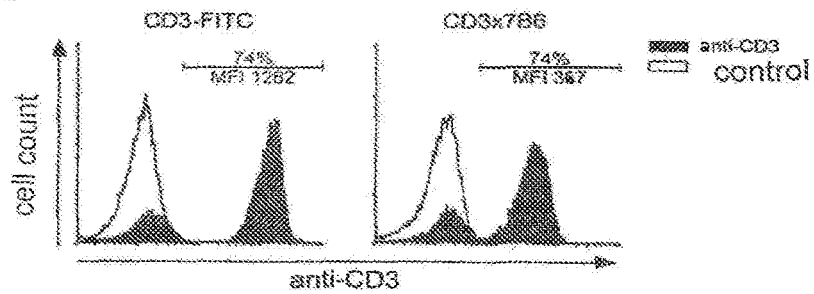
Figure 13E:
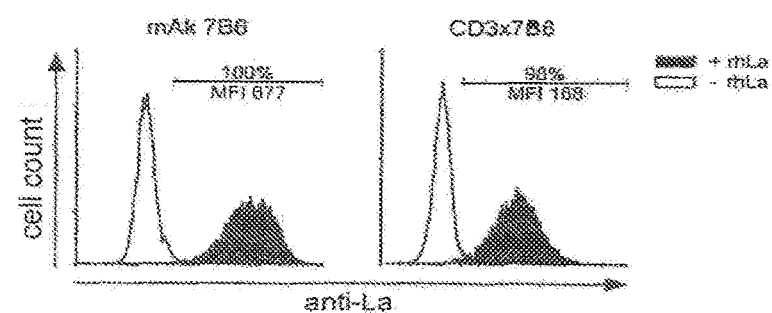

FIG. 13A: The DNA sequence of 7B6 scFv iC was cloned via BamHI restriction sites into the vector pSecTag2 B-CD3 scFv oC in order to obtain the plasmid pSecTag2 B-CD3x7B6 scBsDb. FIG. 13B: The protein CD3x7B6 has an N-terminal Igκ signal peptide which mediates the secretion into the cell culture medium. To the diabody are added C-terminally a c-myc as well as hexahistidine-(His6-) tag to permit the detection of the protein or the purification by Ni-NTA agarose. FIG. 13C: Purification of the eukaryote-produced CD3x7B6 scBsDb. From transduced HEK 293T CD3x7B6 scBsDb cells the supernatent (SN) was removed and applied to an Ni-NTA spin column. The flow (DL) was collected. Subsequently, washing with 10 mM imidazole (W1) and 20 mM imidazole (W2) was carried out. The elution of the diabody was done with 350 mM imidazole (E1-E3). A portion of the cells was taken up in 2×SDS sample buffer (pellet, P) and together with aliquots of all fractions applied onto a 12% polyacrylamide gel. After western blot on a nitrocellulose membrane, CD3x7B6 scBsDb was detected with anti-His and anti-mouse-IgG-AP. Moreover, 10 µl of elution 1 were applied to a second gel which was stained with Coomassie Brilliant Blue (CBB). FIG. 13D: Binding analysis on CD3$^+$ T lymphocytes. As a positive control, the antibody anti-CD3-FITC (black) is shown in comparison to its isotype control. Parallel to this, the PBMCs were incubated with 10 µg CD3x7B6 which was detected with anti-c-myc-FITC (black). As a control, anti-c-myc-FITC was used alone. FIG. 13E: FACS analysis on HEK 293T PSCA cells which had been pretreated with 9 µM of rhLa protein (+rhLa) or without it (−rhLa). The detection of the La protein was done either with mAk 7B6 and anti-mouse-IgG-Alexa Fluor® 488 or with 10 µg CD3x7B6 and anti-c-myc-FITC.

Figure 14:
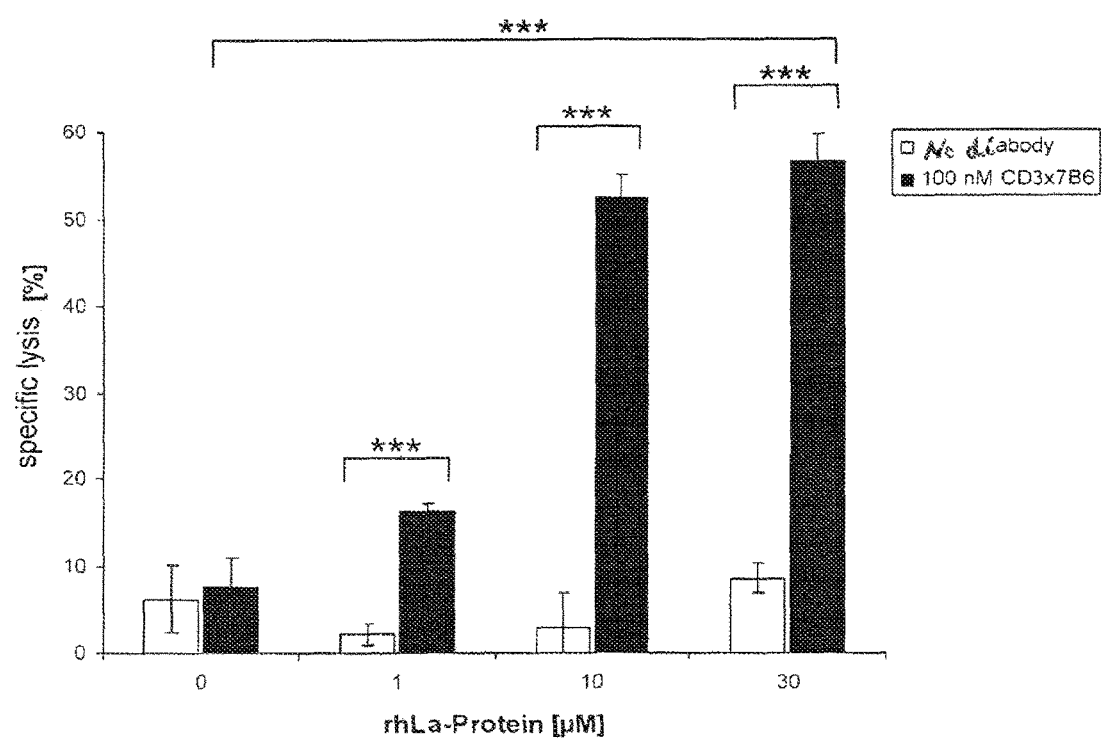

FIG. 14 shows the T cell-mediated cytotoxicity in the presence of CD3x7B6.

For the cytotoxicity test the target cells HEK 293T PSCA were loaded with $^{51}$Cr. Then one quarter of the cells was incubated without La protein or with 1 µM or 30 µM of rhLa protein. Subsequently, the target cells were co-cultured in a ratio of 1:20 with preactivated T cells. Moreover, to some of the samples 100 nM of CD3x7B6 protein was added. After 18 hrs. the chrome release was measured. The average values of a triple determination and their standard deviations are shown. The statistical significance was determined with the Student's t test (***$p<0.001$). A representative donor is shown for three examined ones.

DESCRIPTION OF PREFERRED EMBODIMENTS

Example 1 Binding and Detection of the rhLa Protein on the Cell Surface

For the surface binding studies of the La protein different cell lines as well as PBMCs were examined. The adherent cell lines were seeded in 12-well plates and on the subsequent day incubated with 2-10 µM of rhLa protein in PBS or DMEM. The one-hour La binding took place either on ice or at 37° C. Subsequently, the cells on ice were stained with the anti-La-mAks and a suitable secondary antibody in order to detect the La protein on the cell surface. Then the cells were treated with PFA, Triton X-100 and DAPI solutions before immunofluorescence images were taken. For the quantitative binding studies the stained, unfixed cells were removed with PBS-EDTA and examined flow-cytometrically. Alternatively, the adherent cells were first removed for the flow cytometry with PBS-EDTA and then incubated in a 96-well plate with La and the antibodies.

In the following it was checked how long after decoration the La protein can still be detected on the cells and whether it is perhaps proteolytically cleaved and is only partially present on the cell surface. For this purpose, mouse 3T3 cells were incubated for 1 hr. with rhLa in DMEM at 37° C. Then the medium was changed. The cells were examined either immediately or cultured for another 3 hrs or 24 hrs. At each point in time cells were stained on ice with the different anti-La-mAks 27E, 5B9, SW5 (comparative example), 22A and 7B6 as well as anti-His and a suitable secondary antibody. Subsequently, a portion of the cells was removed with PBS-EDTA from the culture vessels and analyzed in the flow cytometer (see FIG. 11A). Moreover, total extracts of the La-loaded cells and control cells without La protein were produced. Detection with the different antibodies was carried out by western blot (see FIG. 11B).

Example 2 Immunization and Preparation of Hybridomas

For the hybridoma preparation, mice (Balb/C) were immunized with recombinant La protein (rhLa—SEQ ID No. 1 with His tag, 40 mice) produced in *E. coli* BL21 DE3 pLysS and purified by means of nickel-affinity chromatography. 10 other mice were immunized with recombinant rhLa1 192 antigen (La-peptide with amino acid residues from 1 to 192 of the SEQ ID No. 1) produced also in *E. coli* BL21 DE3 pLysS. In the first immunization 50 µg of the respective antigen were applied in complete Freund's adjuvant (Difco, Mich., USA). In the other immunizations, each carried out two weeks apart, 25 µg of antigen were applied in each case. The antigen was for this purpose re-suspended in incomplete adjuvant (Difco, Mich., USA). Before hybridoma fusion, the animals had been immunized four times. After isolation of the spleen cells, they were fused with myeloma cells (P3xAg 8.653; ATCC CRL 1580) in a ratio of 1:1 to 10:1 by dropwise addition of polyethylene glycol. Subsequently, the cells were selected in HAT medium (medium containing hypoxanthine, aminopterin and thymidine). Positive hybridomas were identified by means of ELISA and the cells recloned several times by limited dilution.

In case of the hybridoma fusion of hLa transgenic mice after adoptive transfer of T cells, the protocol was modified as follows. Non-transgenic mice from the same litter were immunized as described above several times with rhLa. Then the spleen cells were prepared and by means of nylon wool the non-adherent cells were isolated. The contaminating B cells were removed by anti-B220 magnetic beads (RA3-6B2, Dynal, Oslo, Norway). The purity of the isolated cells was determined by means of FACS. In the embodiment, 64% of the isolated cells were CD4 positive, 0.76% B220 positive. The remainder consisted of CD8 positive cells. 1x 10$^7$ of these cells were applied intravenously on day zero into the tail vein of a 10 week old hLa transgenic mouse (A/J background). 21 days after the adoptive transfer the spleen was removed and the hybridoma fusion was carried out as described above. By means of ELISA it had been determined before that the anti-La response is optimal between day 21 and day 28 after transfer. Parallel to this, T cells of a non-immunized mouse were transferred into a hLa transgenic mouse. Also, a hybridoma fusion of a control mouse, not immunized, was carried out. Anti-La hybridomas were established only from the mouse that had received adoptive T cells from the La-immunized mouse.

Example 3 Analysis of Hybridoma Supernatents

Recombinant His$_6$ hLa protein was diluted in coating buffer (1-5 µg/ml). Of this, 100 µl were added to every well of the ELISA plate and incubated over night at 4° C. or 2 hrs at 37° C. After washing the plate five times with 200 µl of ELISA washing buffer for each well per washing step, the remaining binding sites were saturated with 200 ,1.1 of ELISA blocking solution, respectively, for 1 hr at 37° C. After washing again, 100 µl of hybridoma supernatent was added to each well of the plate. Binding occurred for 1 hr at 37° C. Subsequently, the non-bound antibodies were removed by washing five times and 100 µl of the diluted secondary antibody anti-mouse-IgG-POD (1:40000 in PBS) were applied to each well. After 1 hr at 37° C. the excess antibodies were removed again by washing. Into each well 100 µl of the substrate solution were pipetted and the plate incubated in the dark. After a distinct color development was recognizable, the reaction was terminated with 50 µl of stop solution per well. The quantification occurred through measurement of the optical density at 450 nm (reference filter 620 nm) by means of an ELISA plate reader.

Example 4 Investigation of the Redox-Dependent Antibody Binding

The ELISA plate was coated with 10 µg/ml rhLa over night at 4° C. This was followed by oxidation (3% (v/v) H$_2$O$_2$ in PBS, 30 min, RT) or reduction (2% (v/v) β-mercapto ethanol in PBS, 30 min, RT) for some of the wells. After blocking the whole plate, incubation with hybridoma supernatents or patients' sera was carried out. The detection was carried out with anti-mouse-IgG-POD or anti-human-IgG-POD.

Example 5 Production of scFv Fragments and Bispecific Antibodies

The production of scFv fragments occurred based on mAk 7B6. Based on the sequences of the V$_H$ and V$_L$ genes which were cloned in pGEM®-T Easy, the scFv derivative was cloned into the vector pSecTag2 B. The suitable recombinant protein (see schematic in FIG. 12A) contains an N-terminal Igx signal sequence which mediates the secretion of the scFv molecules into the cell culture medium and is proteolytically cleaved thereby. The VH and VL domains adjoin it and are connected by a flexible glycine serine linker ((G$_4$S)$_3$) with each other. To the proteins one c-myc tag as well as a hexahistidine tag are added C-terminally in order to enable the specific detection or purification by Ni-NTA affinity chromatography. These eukaryotic expression vectors were transfected into HEK 293T cells. The total extracts of the cells as well as the cell culture supernatents were analyzed with respect to contained anti-La-scFv molecules by immunoblot.

The 7B6 scFv protein was purified by Ni-NTA affinity chromatography from the cell culture medium. The single fractions were examined by western blot which was developed with anti-His in regard to the presence of the recombinant protein. By FACS analyses (see FIG. 12B) binding to cells decorated with rhLa was examined. The La protein was specifically bound by mAk 7B6 as well as by 7B6 scFv. The control cells which had not been pretreated with rhLa protein were not stained in both cases.

Since 7B6 scFv was able to bind the rhLa protein on the cell surface, it was used for the generation of a bispecific CD3x7B6 antibody (single chain bispecific diabody—scBsDb). In the plasmid pSecTag2 B-CD3 scFv oC the variable domains are organized in the sequence V$_H$ CD3-VL CD3 and are connected by a flexible glycine serine linker ((G$_4$S)$_3$) with each other. For the second antigen specificity of the diabody, the inner cassette 7B6 scFv iC (see FIG. 13A, CD scFv iC) with the domain sequence VL 7B6 (G$_4$S) 5-VH 7B6-G$_4$S was inserted into this outer cassette (see FIG. 13A, CD scFv oC). By treatment with the restriction enzyme BamHI the vector pSecTag2 B-CD3 scFv oCc was linearized between V$_H$ CD3 and V$_L$ CD3 and the DNA fragment of 7B6 scFv iC generated in parallel by BamHI was inserted by ligation (see FIG. 13A). The obtained clones were checked by sequencing. Subsequently, the resultant plasmid pSecTag2 B-CD3x7B6 scBsDb was transfected transiently in HEK 293T cells in order to analyze the production and secretion of the CD3x7B6 diabody. As a result of the used vector, the bispecific CD3x7B6 antibody (scBsDb) again has an N-terminal Igx signal sequence, and a c-myc tag and a hexahistidine tag adjoin the protein C-terminally (see FIG. 13B). In order to have at disposal sufficient protein amounts for other experiments, a stable cell line was established by transduction that continuously secrets CD3x7B6 protein. An amplification of the CD3x7B6 DNA sequence by PCR was necessary for this purpose in order to add N-terminally an EcoRI restriction site and C-terminally a Kpn2I restriction site. Finally, by these two restriction enzymes cloning occurred into the retroviral expression vector pczCFG5.1. For the transduction HEK 293T cells were also used as target cells.

The transiently transfected as well as stably transduced HEK 293T cells were capable of producing the CD3x7B6 scBsDb protein and to release it into the cell culture medium. From the latter, it could be obtained by Ni-NTA affinity chromatography (see FIG. 13C). Binding of the protein to CD3+ T lymphocytes was examined on human PBMCs (see FIG. 13D). The protein as well as the antibody anti-CD3-FITC used as a positive control was detected on 74% of the lymphocytes. This proved the functionality of the CD3 arm of the diabody.

Moreover, binding of the CD3x7B6 molecule on rhLa on the cell surface was analyzed. The 7B6 side of the diabody was able to recognize 98% of the cells. This corresponded nearly to 100% of the mAks 7B6 which caused by its bivalent binding, as expected, a stronger shift of the whole cell population in the green fluorescence channel (see FIG. 13E).

Since the CD3x7B6 protein could be detected on La-decorated tumor cells as well as on CD3+ T cells, it can cause a cross-linking between tumor cells and T-effector cells in co-culturing of both cell populations. The cytotoxic T cells are thereby activated and, as a result, the target cells are lysed by them (see schematic in FIG. 9). In order to clarify these effector mechanisms, a chrome release test was carried out. The tumor cells after chrome loading were incubated with different amounts of rhLa protein. Subsequently, they were co-cultured for 18 hrs with preactivated T cells. These T cells are predominantly CD8+ cytotoxic T cells which were obtained by incubation of PBMCs with IL-2 and anti-CD3 (OKT3). This protocol was developed at the Institut für Immunologie and the obtained T cells have been characterized in detail. The results of the chrome release test are shown in FIG. 14.

For the cytotoxicity test the target cells HEK 293T PSCA were loaded with $^{51}$Cr. Then one quarter of the cells was incubated without La protein or with 1 μM, 10 μM or 30 μM of rhLa protein, respectively. Subsequently, the target cells were co-cultured in a ratio 1:20 with preactivated T cells. Moreover, to a part of the batches 100 nM of CD3x7B6 protein was added. After 18 hrs the chrome release was measured. The average values of a triple determination and their standard deviations are shown. The statistical significance was determined by Student's t test (*** p<0.001). A representative donor is shown for three examined ones.

What is claimed is:

1. Recombinant antibody, comprising
   (a) a binding unit of a first antibody that specifically binds to an epitope of a human nuclear antigen, wherein one such human nuclear antigen can comprise human La, characterized in that the first antibody is an antibody which binds specifically an epitope of the human La protein (anti-La antibody) containing regions determining complementarity (complementarity determining regions, CDRs), the CDRs of the variable region of the light chain (V L) and the variable region of the heavy chain (V H) comprising the following sequences:

|  | $V_L$ | SEQ ID No. | $V_H$ | SEQ ID No. |
|---|---|---|---|---|
| CDR1 | RSSQSLLDSRTRKNYLA | 9 | DFWMN | 10 |
| CDR2 | WASTRES | 11 | QIRNKPNNYETYYSDSLKG | 12 |
| CDR3 | KQSYNLPT | 13 | LGNSWFAY | 14 | and
   (b) a binding unit comprising:
      a second antibody which binds specifically to an effector cell or
      a ligand which binds specifically to an effector cell.

2. The recombinant antibody according to claim 1, characterized in that the second antibody or the ligand which binds specifically to an effector cell is selected from antibodies and ligands which bind specifically surface structures on T lymphocytes, NK cells and/or monocytes.

3. The recombinant antibody according to claim 1 containing the following, optionally humanized, structure:
   a variable region of the light chain having a sequence of SEQ ID No. 53 and
   a variable region of the heavy chain having a sequence of SEQ ID No. 54.

4. The recombinant antibody according to claim 1, in the form of a scFv fragment, a F(ab')$_2$ fragment, diabodies, triabodies or tetrabodies.

5. Antibodies which bind specifically an epitope of the human La protein (anti-La antibody) containing regions determining complementarity (complementarity determining regions, CDRs), characterized in that the CDRs of the variable region of the light chain ($V_L$) and the variable region of the heavy chain ($V_H$) comprise the following sequences:

|  | $V_L$ | SEQ ID No. | $V_H$ | SEQ ID No. |
|---|---|---|---|---|
| CDR1 | RSSQSLLDSRTRKNYLA | 9 | DFWMN | 10 |
| CDR2 | WASTRES | 11 | QIRNKPNNYETYYSDSLKG | 12 |
| CDR3 | KQSYNLPT | 13 | LGNSWFAY | 14 |

6. The antibodies according to claim 5, containing the following, optionally humanized, structure:

a variable region of the light chain having a sequence of SEQ ID No. 53 and a variable region of the heavy chain having a sequence of SEQ ID No. 54.

7. The antibodies according to claim 5 in the form of a scFv fragment, a F(ab')$_2$ fragment, diabodies, triabodies or tetrabodies.

\* \* \* \* \*